US012737041B2

(12) United States Patent
Lozada et al.

(10) Patent No.: US 12,737,041 B2
(45) Date of Patent: Sep. 15, 2026

(54) USER INTERACTIONS AND EYE TRACKING WITH TEXT EMBEDDED ELEMENTS

(71) Applicant: APPLE INC., Cupertino, CA (US)

(72) Inventors: Richard Ignatius Punsal Lozada, Cupertino, CA (US); Anshu K. Chimalamarri, Sunnyvale, CA (US); Bryce L. Schmidtchen, San Francisco, CA (US); Gregory Lutter, Boulder Creek, CA (US); Paul Ewers, San Jose, CA (US); Peter Burgner, Venice, CA (US); Thomas J. Moore, Northglenn, CO (US); Trevor J. McIntyre, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/731,616

(22) Filed: Jun. 3, 2024

(65) Prior Publication Data

US 2024/0319789 A1 Sep. 26, 2024

Related U.S. Application Data

(63) Continuation of application No. PCT/US2022/052237, filed on Dec. 8, 2022.

(Continued)

(51) Int. Cl.

*G06F 3/01* (2006.01)
*A61B 5/16* (2006.01)

(52) U.S. Cl.

CPC .............. *G06F 3/013* (2013.01); *A61B 5/163* (2017.08)

(58) Field of Classification Search

CPC ................................ G06F 3/013; A61B 5/163
See application file for complete search history.

(56) References Cited

U.S. PATENT DOCUMENTS

| | | | |
|---|---|---|---|
| 5,731,805 A | 3/1998 | Tognazzini | |
| 6,127,990 A * | 10/2000 | Zwern | G09B 9/00 345/158 |

(Continued)

FOREIGN PATENT DOCUMENTS

| | | |
|---|---|---|
| CN | 111400595 A | 7/2020 |
| WO | 2020208302 A1 | 10/2020 |

OTHER PUBLICATIONS

European Patent Office (ISA/EP), International Search Report and Written Opinion of the International Searching Authority, International Application No. PCT/US2022/052237, 14 pages, Apr. 24, 2023.

*Primary Examiner* — Mihir K Rayan
(74) *Attorney, Agent, or Firm* — Thompson Hine LLP

(57) ABSTRACT

Various implementations disclosed herein include devices, systems, and methods that determine whether the user is reading text or intends an interaction with a portion of the text in order to initiate an interaction event during the presentation of the content. For example, an example process may include obtaining physiological data associated with an eye of a user during presentation of content, wherein the content includes text, determining whether the user is reading a portion of the text or intends an interaction with the portion of the text based on an assessment of the physiological data with respect to a reading characteristic, and in accordance with a determination that the user intends the interaction with the portion of the text, initiating an interaction event associated with the portion of the text.

20 Claims, 9 Drawing Sheets

Related U.S. Application Data

(60) Provisional application No. 63/289,322, filed on Dec. 14, 2021.

(56) References Cited

U.S. PATENT DOCUMENTS

| | | | | |
|---|---|---|---|---|
| 8,824,779 | B1 | 9/2014 | Smyth | |
| 8,994,613 | B1 | 3/2015 | Johnson | |
| 9,478,143 | B1* | 10/2016 | Bowen | G09B 5/062 |
| 10,884,577 | B2 | 1/2021 | Palti-Wasserman | |
| 2013/0232444 | A1* | 9/2013 | Hegde | G06F 3/0485<br>715/785 |
| 2014/0049452 | A1* | 2/2014 | Maltz | G02B 27/017<br>345/8 |
| 2014/0186806 | A1* | 7/2014 | Hallowell | G09B 19/04<br>434/167 |
| 2015/0212576 | A1* | 7/2015 | Ambrus | G06F 3/0482<br>345/156 |
| 2015/0213634 | A1* | 7/2015 | Karmarkar | G06V 40/18<br>345/589 |
| 2016/0252956 | A1 | 9/2016 | Wheeler | |
| 2018/0004287 | A1* | 1/2018 | Yoo | G06F 3/0482 |
| 2018/0300008 | A1* | 10/2018 | Rasanen | G06F 3/04886 |
| 2020/0160744 | A1* | 5/2020 | Sipolins | G06F 3/015 |
| 2021/0157402 | A1 | 5/2021 | Parshionikar | |
| 2022/0261073 | A1* | 8/2022 | Francis | G06F 3/017 |
| 2023/0144091 | A1* | 5/2023 | Forutanpour | G06F 3/011<br>345/156 |

* cited by examiner 400
432
Coffee
Tea
Espresso
434
Large
Medium
Small
436
Whole Milk
Half & Half
Soy Milk
25
10
515A
512A
552
525
520
522
524

515B
512B
554
530
535
532
534
L
M
S

502
... with soy milk please
515C
512C
556
545

USER INTERACTIONS AND EYE TRACKING WITH TEXT EMBEDDED ELEMENTS

CROSS-REFERENCE TO RELATED APPLICATIONS

This patent application is a continuation of International Application No. PCT/US2022/052237 filed Dec. 8, 2022, which claims the benefit of U.S. Provisional Application No. 63/289,322 filed Dec. 14, 2021, entitled "USER INTERACTIONS AND EYE TRACKING WITH TEXT EMBEDDED ELEMENTS," each of which is incorporated herein by this reference in its entirety.

TECHNICAL FIELD

The present disclosure generally relates to presenting content via electronic devices, and in particular, to systems, methods, and devices that determine an intent of a user during and/or based on the presentation of electronic content and physiological data of the user.

BACKGROUND

Determining a user's intent while viewing content on an electronic device can facilitate a more meaningful experience. For example, a portion of the text (e.g., a selectable icon or button) may be automatically selected based on determining the user's intent to make such a selection and without the user necessarily having to perform a gesture, mouse click, or other input-device-based action to initiate the selection. Improved techniques for assessing the intent of users viewing and interacting with content may enhance the users' enjoyment, comprehension, and learning of the content. Content creators and systems may be able to provide better and more tailored user experiences based on determining user intent to interact with portions of the text.

SUMMARY

Various implementations disclosed herein include devices, systems, and methods that assess physiological data (e.g., gaze characteristic(s)) and reading characteristics of a user viewing/reading content to predict an interaction event (e.g., predicting whether the user is reading the text and intends an interaction with the portion of the text). For example, a method may identify, during a particular segment of the experience, the user's gaze characteristics (e.g., pupil dilation vs. constriction, stable gaze direction, and/or velocity) and use those characteristics in determining whether the user is reading, determining a reading pace, determining whether the user is focused on a particular element and for how long, and the like. As examples, this may involve detecting the user is transitioning from reading to interacting with a portion of the text, or detecting that the user is immediately interacting with the portion of the text instead of reading.

In some implementations, algorithms and/or machine learning models may be configured/refined based on (e.g., learning from) user specific actions. For example, user actions may include the user's actual reading pace, the user's actual/confirmed transitions from reading to interaction, or the user's canceling of auto-triggered interactions (e.g., indicating a false activation). Additionally, user actions may include a user's negative response to an auto-triggered interaction, such as eye twitch, eye closing, and/or squinting (e.g., indicating a false activation).

Physiological data may be used to determine whether to initiate an interaction event during the presentation of the content based on determining whether the user is reading the text or intends an interaction with the portion of the text. For example, some implementations may identify that the user's eye characteristics (e.g., blink rate, stable gaze direction, saccade amplitude/velocity, and/or pupil radius) relate to an interaction with a presentation of an interaction element (e.g., an icon) based on those eye characteristics differing from eye characteristics associated with reading. For example, the user's gaze may move in a way that corresponds to reading. Additionally, the user's eye characteristics may be analyzed to determine that the user's gaze movement corresponds to an average reading pace or a reading pace that is associated with the specific user. Additionally, determining the user's characteristics may involve obtaining images of the eye or electrooculography (EOG) data, sensor data corresponding to microsaccades, and/or sensor data corresponding to head movements, from which pupil response/gaze direction/movement or other user characteristics can be determined.

Context may additionally be used to determine interaction events. For example, a scene analysis of an experience can determine a scene understanding of the visual and/or auditory attributes associated with content being presented to the user (e.g., what is being presented in video content while the user is reading text) and/or attributes associated with the environment of the user (e.g., where is the user, what is the user doing, what objects are nearby). These attributes of both the presented content and environment of the user can improve the determination of the user's intent regarding an interaction event.

In some implementations, determining whether to initiate an interaction event may be based on a characteristic of an environment of the user (e.g., real-world physical environment, a virtual environment, or a combination of each). The device (e.g., a handheld, laptop, desktop, or head-mounted device (HMD)) provides an experience (e.g., a visual and/or auditory experience) of the real-world physical environment or an extended reality (XR) environment. The device obtains, with one or more sensors, physiological data (e.g., electroencephalography (EEG) amplitude, pupil modulation, eye gaze saccades, head movements measured by an inertial measurement unit (IMU), etc.) associated with the user. Based on the obtained physiological data, the techniques described herein can determine an interaction event during the experience. Based on the physiological data and associated physiological response (e.g., a user focusing on a particular region of the content), the techniques can provide a response to the user based on the interaction event and adjust the content corresponding to the experience.

Physiological data, such as EEG amplitude/frequency, sensor data corresponding to pupil modulation, sensor data corresponding to eye gaze saccades, etc., can depend on the individual, characteristics of the scene in front of him or her (e.g., video content), and attributes of the physical environment surrounding the user including the activity/movement of the user. Physiological data can be obtained while using a device with eye tracking technology (and other physiologic sensors) while users perform tasks. In some implementations, physiological data can be obtained using other sensors, such as EEG sensors or EDA sensors. Observing repeated measures of physiological data to an experience can give insights about the intent of the user.

Several different experiences can utilize the techniques described herein regarding assessing interaction events based on whether the user is reading. For example, the method can be provided to support users who want to interact with portions of the text without using hands, voice, or overt eye movements like dwell time. Additionally, determining interaction events based on reading characteristics can be used as an accessibility feature, for example, that enables paralyzed users to interact by selecting computer graphic icons using their eyes while reading. Additionally, determining interaction events can be used in general applications (e.g., a user interface selection tool, a device wake-up signal, etc.), and might be combined with other eye or touch-based mechanisms, such as to improve signal-to-noise ratio (SNR), robustness, response time, and the like.

Some implementations focus on improving the accuracy for determining whether to initiate an interaction event during the presentation of the content based on determining whether the user is reading the text or intends to have an interaction with the portion of the text by incorporating practice exercises. For example, a machine learning algorithm may be implemented to determine whether or not a user's reading characteristics (e.g., determining whether the user is reading, determining a reading pace, determining whether the user is focused on a particular element and for how long, and the like) means that he or she is intending to select/interact with a particular portion of the text (e.g., selecting a particular menu item).

Some implementations assess physiological data and other user information to help improve a user experience. In such processes, user preferences and privacy should be respected, as examples, by ensuring the user understands and consents to the use of user data, understands what types of user data are used, has control over the collection and use of user data and limiting distribution of user data, for example, by ensuring that user data is processed locally on the user's device. Users should have the option to opt in or out with respect to whether their user data is obtained or used or to otherwise turn on and off any features that obtain or use user information. Moreover, each user should have the ability to access and otherwise find out anything that the system has collected or determined about him or her.

In general, one innovative aspect of the subject matter described in this specification can be embodied in methods that include the actions of obtaining physiological data associated with an eye of a user during presentation of content, where the content includes text, determining whether the user is reading a portion of the text or intends an interaction with the portion of the text based on an assessment of the physiological data with respect to a reading characteristic, and in accordance with a determination that the user intends the interaction with the portion of the text, initiating an interaction event associated with the portion of the text.

These and other embodiments can each optionally include one or more of the following features.

In some aspects, the interaction event is embedded within the portion of the text. In some aspects, in accordance with a determination that the user is reading the portion of the text, the method further includes forgoing initiating the interaction event associated with the portion of the text. In some aspects, the reading characteristic includes a reading pace of the text by the user.

In some aspects, determining whether the user is reading the portion of the text or intends an interaction with the portion of the text based on the assessment includes determining a transition detection from the user reading the text to the user intending the interaction with the portion of the text.

In some aspects, determining whether the user is reading a portion of the text or intends an interaction with the portion of the text based on the assessment includes determining a reading pace of the user from the user reading the text, and comparing the reading pace to a threshold.

In some aspects, determining whether the user is reading a portion of the text or intends an interaction with the portion of the text based on the assessment includes detecting that the user is transitioning from reading the portion of the text to interacting with the portion of the text.

In some aspects, determining whether the user is reading a portion of the text or intends an interaction with the portion of the text based on an assessment includes determining scene-induced pupil response variation characteristics for the portion of the text, and determining that the user intends an interaction with the portion of the text based on the scene-induced pupil response variation characteristics for the portion of the text.

In some aspects, an intent for the interaction is classified using a machine learning technique based on the pupillary response and the reading characteristic.

In some aspects, the machine learning technique is refined based on at least one of a reading pace of the user, a detected transition from reading the text to an intent to interact with the portion of the text, and a detected intent of the user to cancel an interaction event.

In some aspects, the method further includes adjusting content in response to initiating the interaction event.

In some aspects, the method further includes determining that the user cancels the interaction event based on determining that the interaction event includes a false positive activation based on a detection of an abnormal user action.

In some aspects, the abnormal user action is an eye twitch, an eye closing, or an eye squinting.

In some aspects, the physiological data includes an image of an eye or electrooculography (EOG) data. In some aspects, the physiological data includes head movements of the user.

In some aspects, the device is a head-mounted device (HMD). In some aspects, the presentation of content is an extended reality (XR) experience that is presented to the user.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 2:
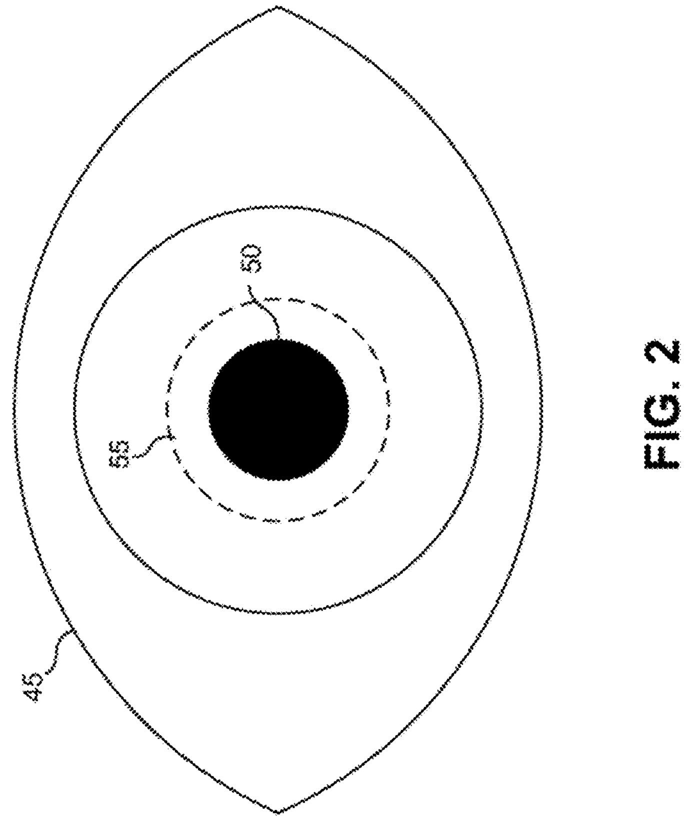
FIG. 2 illustrates a pupil of the user of FIG. 1 in which the diameter of the pupil varies with time in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

Figure 1:
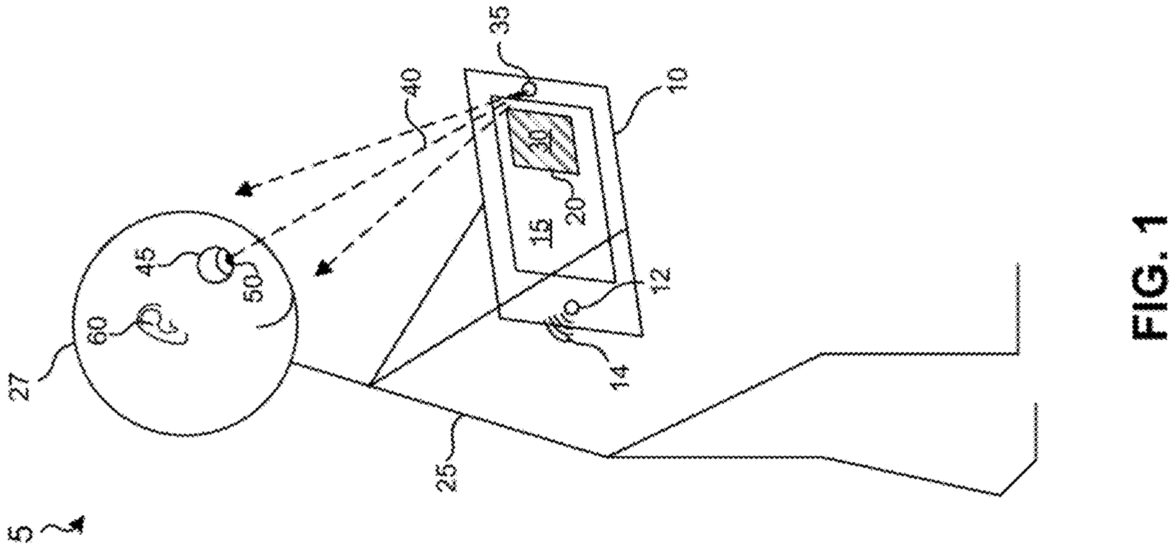
FIG. 1 illustrates a device presenting a visual and/or auditory experience and obtaining physiological data from a user in accordance with some implementations.

FIG. 1 illustrates a real-world environment 5 including a device 10 with a display 15. In some implementations, the device 10 displays content 20 to a user 25, and a visual characteristic 30 that is associated with content 20. For example, content 20 may be a button, a user interface icon, a text box, a graphic, etc. In some implementations, the visual characteristic 30 associated with content 20 includes visual characteristics such as hue, saturation, size, shape, spatial frequency, motion, highlighting, etc. For example, content 20 may be displayed with a visual characteristic 30 of green highlighting covering or surrounding content 20.

In some implementations, content 20 may be a visual experience (e.g., an education experience), and the visual characteristic 30 of the visual experience may continuously change during the visual experience. As used herein, the phrase "experience" refers to a period of time during which a user uses an electronic device and has one or more interaction events. In one example, a user has an experience in which the user perceives a real-world environment, virtual content, or both, while holding, wearing, or being proximate to an electronic device that includes one or more sensors that obtain physiological data that is indicative of the user's interaction event. In another example, a user has an experience in which the user perceives content displayed by an electronic device while the same or another electronic device obtains physiological data (e.g., pupil data, EEG data, head movements, etc.) to assess the user's interaction with an interaction element (e.g., a selectable icon). The physiological data may include, but is not limited to, pupil data, EEG data, head movement data, gaze speed, blink rate, raw eye images, eye-lid shape, micro saccades, eye tremor, eye drift, and the like. In another example, a user has an experience in which the user holds, wears, or is proximate to an electronic device that provides a series of audible or visual instructions that guide the experience. For example, the instructions may instruct the user to have particular interaction events during particular time segments of the experience, e.g., instructing the user to focus on his or her attention to a particular portion of the interaction element in order to further train a machine learning algorithm to better detect the user intentions of selecting the interaction element. During such an experience, the same or another electronic device may obtain physiological data to assess the user's intent to interact with the interaction element.

In some implementations, the visual characteristic 30 is a feedback mechanism for the user that is specific to the experience (e.g., a visual or audio cue to focus on a particular task during an experience, such as reading a particular part of an education/learning experience). In some implementations, the visual experience (e.g., content 20) can occupy the entire display area of display 15. For example, during an experience, content 20 may be a video or sequence of images that may include visual and/or audio cues as the visual characteristic 30 presented to the user to pay attention. Other visual experiences that can be displayed for content 20 and visual and/or audio cues for the visual characteristic 30 will be further discussed herein.

The device 10 obtains physiological data (e.g., EEG amplitude/frequency, pupil modulation, eye gaze saccades, etc.) from the user 25 via a sensor 35 (e.g., one or more camera's facing the user to capture light intensity data and/or depth data of a user's facial features, head movements, and/or eye gaze). For example, the device 10 obtains pupillary data 40 (e.g., eye gaze characteristic data). In some implementations, head movements of the user 25 may be obtained by sensor(s) 35 as illustrated. Alternatively, head movements may be obtained by another sensor that the user 25 is wearing. For example, if the device 10 is worn on the head (e.g., an HMD), then the head movements of the user 25 may be determined by an IMU, or another type of accelerometer sensor.

In some implementations, the device 10 includes an eye tracking system for detecting eye position and eye movements. For example, an eye tracking system may include one or more infrared (IR) light-emitting diodes (LEDs), an eye tracking camera (e.g., near-IR (NIR) camera), and an illumination source (e.g., an NIR light source) that emits light (e.g., NIR light) towards the eyes of the user 25. Moreover, the illumination source of the device 10 may emit NIR light to illuminate the eyes of the user 25 and the NIR camera may capture images of the eyes of the user 25. In some implementations, images captured by the eye tracking system may be analyzed to detect position and movements of the eyes of the user 25, or to detect other information about the eyes such as pupil dilation or pupil diameter. Moreover, the point of gaze estimated from the eye tracking images may enable gaze-based interaction with content shown on the near-eye display of the device 10.

In some implementations, the device 10 has a graphical user interface (GUI), one or more processors, memory and one or more modules, programs or sets of instructions stored in the memory for performing multiple functions. In some implementations, the user 25 interacts with the GUI through finger contacts and gestures on the touch-sensitive surface. In some implementations, the functions include image editing, drawing, presenting, word processing, website creating, disk authoring, spreadsheet making, game playing, telephoning, video conferencing, e-mailing, instant messaging, workout support, digital photographing, digital videoing, web browsing, digital music playing, and/or digital video playing. Executable instructions for performing these functions may be included in a computer readable storage medium or other computer program product configured for execution by one or more processors.

In some implementations, the device 10 employs various physiological sensor, detection, or measurement systems. Detected physiological data may include, but is not limited to, EEG, electrocardiography (ECG), electromyography (EMG), functional near infrared spectroscopy signal (fNIRS), blood pressure, skin conductance, or pupillary response. The device 10 maybe communicatively coupled to an additional sensor. For example, an external sensor (e.g., an EDA sensor) maybe communicatively coupled to device 10 via a wired or wireless connection, and the external sensor may be located on the skin of the user 25 (e.g., on the user's arm, or placed on the hand/fingers of the user). For example, the sensor can be utilized for detecting EDA (e.g., skin conductance), heart rate, or other physiological data that utilizes contact with the skin of a user. Moreover, the device 10 (using one or more sensors) may simultaneously detect multiple forms of physiological data in order to benefit from synchronous acquisition of physiological data. Moreover, in some implementations, the physiological data represents involuntary data, e.g., responses that are not under conscious control. For example, a pupillary response may represent an involuntary movement.

In some implementations, one or both eyes 45 of the user 25, including one or both pupils 50 of the user 25 present physiological data in the form of a pupillary response (e.g., pupillary data 40). The pupillary response of the user 25 results in a varying of the size or diameter of the pupil 50, via the optic and oculomotor cranial nerve. For example, the pupillary response may include a constriction response (miosis), e.g., a narrowing of the pupil, or a dilation response (mydriasis), e.g., a widening of the pupil. In some implementations, the device 10 may detect patterns of physiological data representing a time-varying pupil diameter.

In some implementations, a pupillary response may be in response to an auditory feedback that one or both ears 60 of the user 25 detect (e.g., an audio notification to the user). For example, device 10 may include a speaker 12 that projects sound via sound waves 14. The device 10 may include other audio sources such as a headphone jack for headphones, a wireless connection to an external speaker, and the like.

FIG. 2 illustrates a pupil 50 of the user 25 of FIG. 1 in which the diameter of the pupil 50 varies with time. Pupil diameter tracking may be potentially indicative of a physiological state of a user. As shown in FIG. 2, a present physiological state (e.g., present pupil diameter) may vary in contrast to a past physiological state (e.g., past pupil diameter 55). For example, the present physiological state may include a present pupil diameter and a past physiological state may include a past pupil diameter.

The physiological data may vary in time and the device 10 may use the physiological data to measure one or both of a user's physiological response to the visual characteristic 30 (e.g., reading text) or the user's intention to interact with content 20. For example, when presented with content 20, which may include an interactive element, by a device 10, the user 25 may select the interactive element without requiring the user 25 to complete a physical button press. In some implementations, the physiological data may include the physiological response of a visual or an auditory stimulus of a radius of the pupil 50 after the user 25 glances at content 20, measured via eye-tracking technology (e.g., via a HMD). In some implementations, the physiological data includes EEG amplitude/frequency data measured via EEG technology, or EMG data measured from EMG sensors or motion sensors.

Figure 3A:
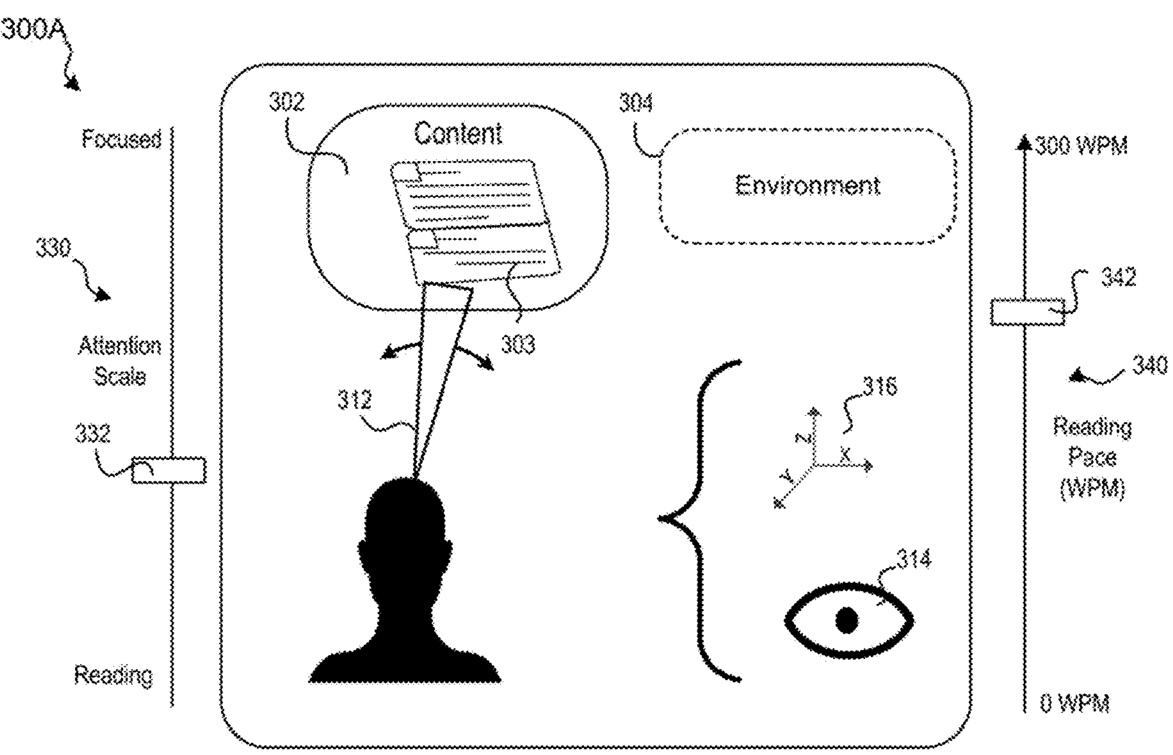
FIGS. 3A and 3B illustrate detecting an interaction event of the user viewing content based on physiological data in accordance with some implementations.
Figure 3B:
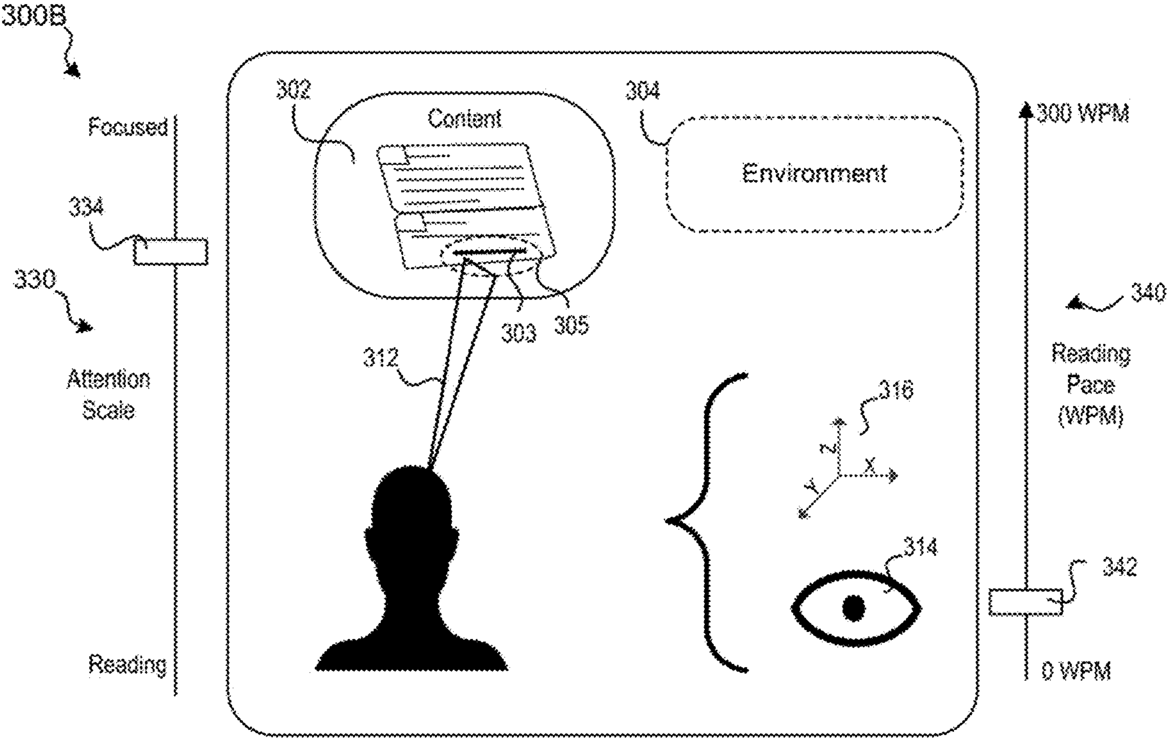

FIGS. 3A and 3B illustrate assessing whether there is an interaction event of the user viewing content based on physiological data and associated reading characteristics. FIG. 3A illustrates a user (e.g., user 25 of FIG. 1) being presented with content 302 in an environment 304 during a content presentation where the user, via obtained physiological data, has a physiological response to the content (e.g., the user looks towards portions of the content as detected by eye gaze characteristic data 312). For example, at content presentation instant 300A, a user is being presented with content 302 that includes visual content (e.g., text), and the user's physiologic data such as pupillary data 312 (e.g., eye gaze characteristic data) is monitored. FIG. 3B illustrates a similar example as FIG. 3A, except that the user focuses his or her gaze upon the interactive element 303 (e.g., the user wants to select the text, such as an embedded interactable icon, being presented to him or her), as illustrated at selection notification 305. Therefore, the content 302 may be updated based on the interaction/focus of the user upon the interactive element 303 (e.g., the user wants to select the embedded interactable icon represented by interactive element 350).

In the particular examples of FIGS. 3A and 3B, at content presentation instant 300A, the user's eye gaze characteristic is less focused on the content 302, such that the attention scale 330 shows the sliding bar indicator 332 as lower towards the "reading" portion, and a higher reading pace (e.g., via reading pace scale 340 showing the sliding bar indicator 342 at a higher rate). Then, at content presentation instant 300B of FIG. 3B (e.g., during a focused stage), the user's eye gaze characteristic 312 appears to be focused on the interactive element 303 of the content 302, such that the attention scale 330 shows the sliding bar indicator 334 as higher towards the "focused" portion, and a lower reading pace on the reading pace scale 340 then at content presentation instant 300A. For example, the reading pace scale 340 is based on words per minute (WPM), such that as the reading pace gets closer to zero, then the system can determine that the user's gaze may be focused upon a particular area or text, and is no longer reading the text, but wants to select the text.

Figure 4:
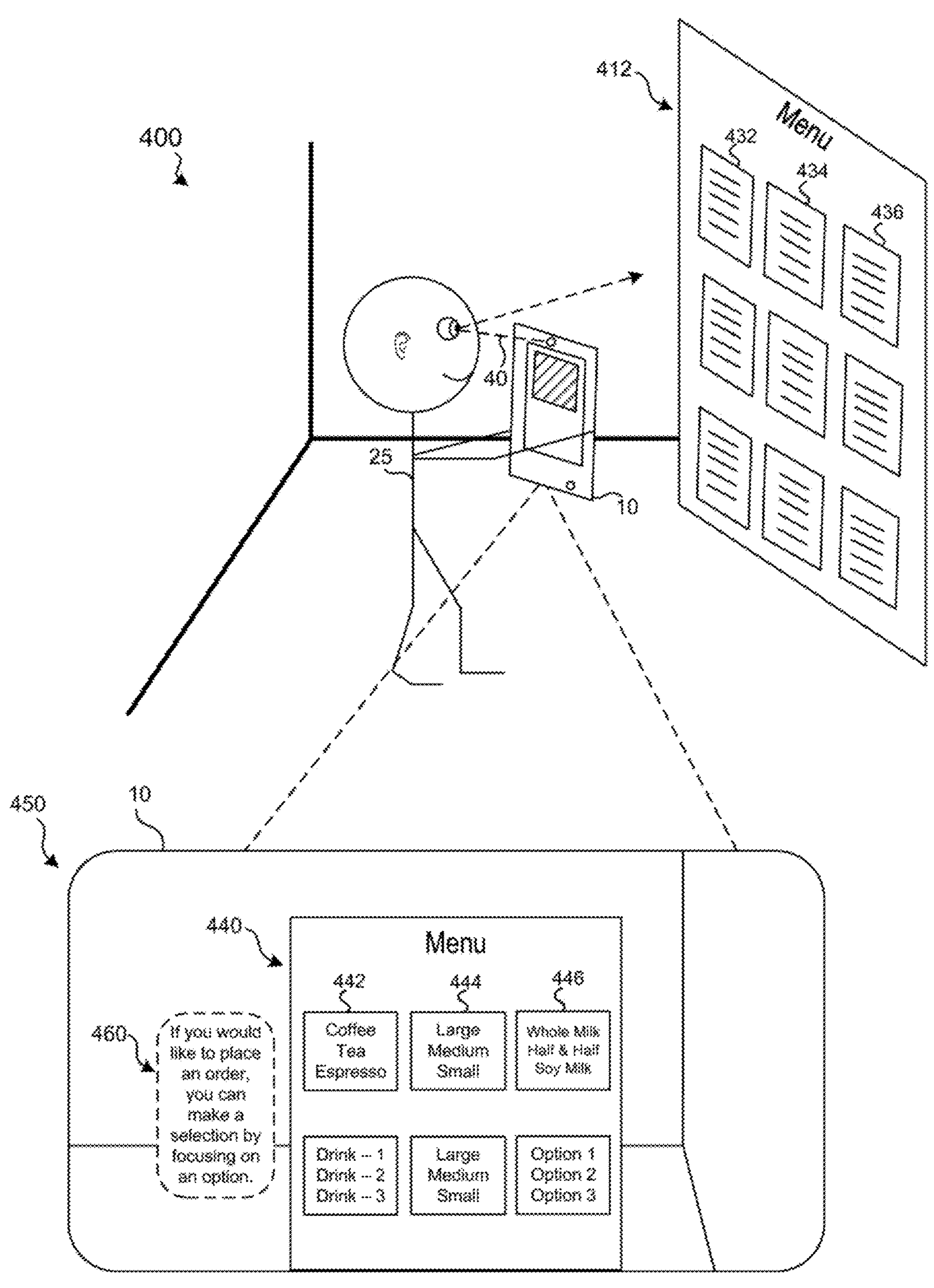
FIG. 4 illustrates an exemplary view of the electronic device of FIG. 1 in accordance with some implementations.

FIG. 4 illustrates an exemplary view 450 of the physical environment 400 provided by electronic device 10. The physical environment 400 includes a menu 412 (e.g., on a wall or a display panel) that includes a first portion 432, a second portion 434, and a third portion 436. The view 450 may be a live camera view of the physical environment 400, a view of the physical environment 400 through a see-through display, or a view generated based on a 3D model corresponding to the physical environment 400. The view 450 includes depictions of aspects of a physical environment 400 such as a representation 440 of menu 412. Within the view of representation 440 of menu 412 is the representation 442 of the first portion 432, representation 444 of the second portion 434, and representation 446 of the third portion 436 of the menu 412.

Additionally, the view 450 includes virtual content that is overlayed on representations of the physical environment 400. In some implementations, systems and techniques described herein can detect whether text that is presented is selectable (e.g., an interactive element). For example, notification 460 may be displayed to indicate to the user that the representation 440 of menu 412 may allow a user to read and select particular items (as further described herein with references to FIGS. 5A-5C).

In some implementations, the techniques described herein can utilize a training or calibration sequence to adapt to the specific physiological characteristics of a particular user 25. In some implementations, the techniques present the user 25 with a training scenario in which the user 25 is instructed to interact (e.g., focus) with some particular text (e.g., interactive text). For example, the notification 460 may provide the user instructions to focus on particular portions of the menu to train a machine learning algorithm. For example, the notification 460 may instruct the user to locate and focus on the word "Coffee" in the representation 442 of the first portion 432 (e.g., for a predefined length of time, such as three seconds, or a user-defined length of time that is representative of their intent to interact with the text), then locate and focus on the word "Medium" in the representation 444 of the second portion 434 (e.g., for a predefined length of time, such as three seconds, or a user-defined length of time that is representative of their intent to interact with the text), and finally locate and focus on the word "Soy Milk" in the representation 446 of the third portion 436 (e.g., for a predefined length of time, such as three seconds, or a user-defined length of time that is representative of their intent to interact with the text). By providing the user 25 with a known intent or area of interest (e.g., via instructions), the techniques can record the user's physiological data (e.g., pupillary data 40) and identify a pattern associated with the user's physiological data.

Moreover, the techniques can change or alter the text in order to identify a pattern associated with the user's physiological response to the altered text. In some implementations, the pattern associated with the physiological response of the user 25 is stored in a user profile associated with the user and the user profile can be updated or recalibrated at any time in the future (e.g., storing a reading pace for each user). For example, the user profile could automatically be modified over time during a user experience to provide a more personalized user experience (e.g., a personal educational experience for optimal learning experience while studying). In some implementations, a "click" threshold may be utilized for training a machine learning model. For example, a "click" threshold may be increased or decreased in real-time to maximize true positive events and minimize false positives. Additionally, or alternatively, in some implementations, implicit feedback from the user (e.g., if a sequence of interactions indicates one interaction was an error) may be used to determine true versus false positives in real-time and the "click" threshold may be adapted by the system accordingly. In some implementations, the techniques described herein can utilize a training process or calibration sequence to involve "gamification", where the user learns to achieve a certain task over time where there is an animation that corresponds to the real-time output of a machine learning model prediction about the probability of click. For example, controlling and closing a ring animation, where the ring closes in proportion to the model's predicated click probability.

Figures 5A, 5B, 5C:
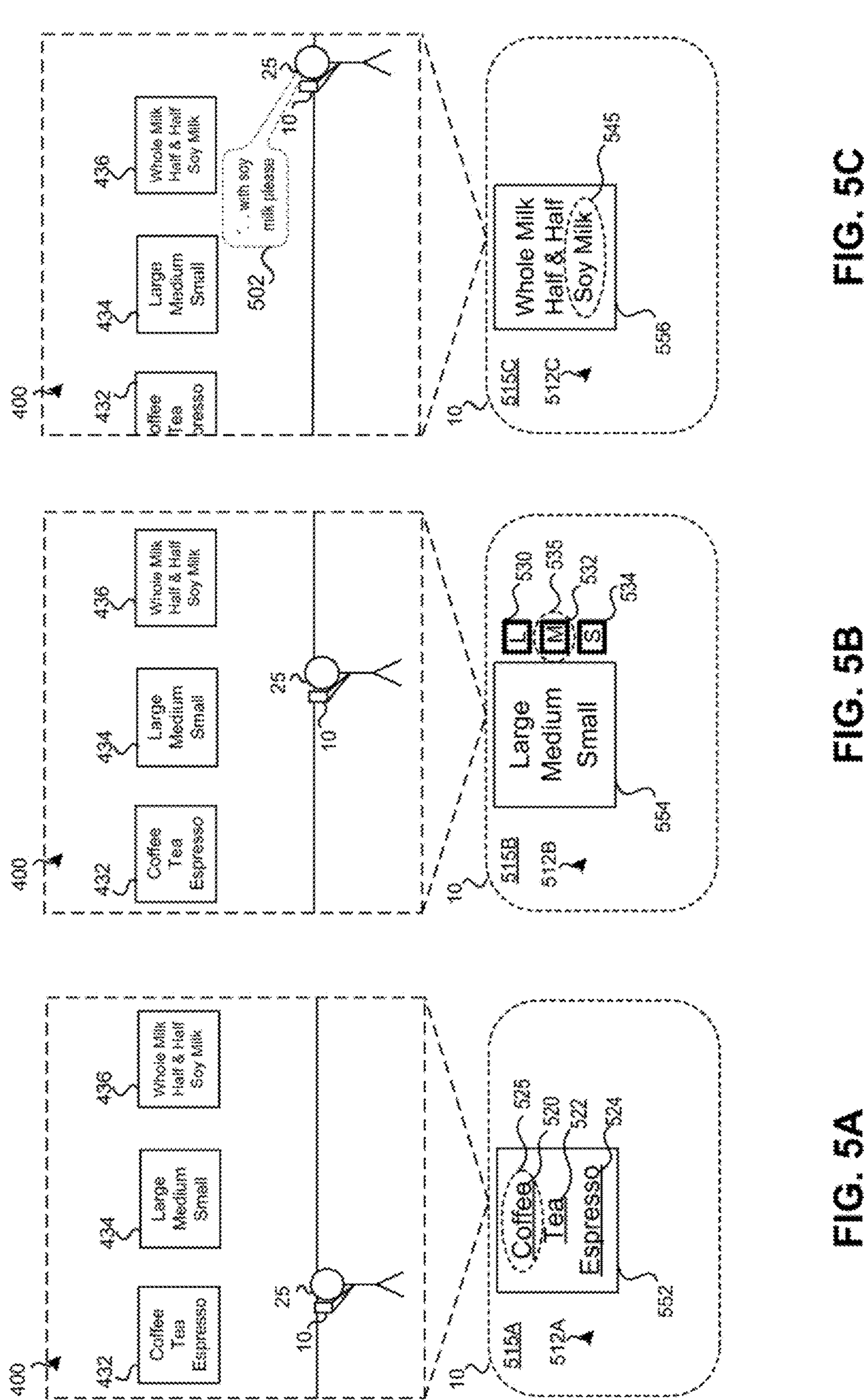
FIGS. 5A, 5B, and 5C illustrate exemplary views of an electronic device with interactable elements embedded within text, in accordance with some implementations.

FIGS. 5A-5C illustrate exemplary views of an electronic device with interactable elements embedded within text, in accordance with some implementations. In some implementations, each view is of an XR environment that includes a representation of at least a portion of the physical environment, such as ordering from a menu 412 in environment 400 of FIG. 4, in accordance with some implementations. For instance, FIGS. 5A-5C illustrate an exemplary electronic device 10 providing view 515A of 3D environment 512A, view 515B of 3D environment 512B, and view 515C of 3D environment 512C, respectively, operating in the same physical environment 400 as FIG. 4 during a viewing of content (e.g., reading/ordering from menu 412). For example, FIGS. 5A-5C may represent an ordering session at three different periods of time while the user focuses on particular text on the menu 412 to place in order in the physical environment 400. In particular, FIG. 5A, for a first period of time, illustrates user 25 standing in front of and looking at (e.g., focusing on, such as eye gaze and head movement) the first portion 432 of the menu 412 (e.g., ordering coffee, tea, or expresso). FIG. 5B, for a second period of time, illustrates user 25 standing in front of and looking at the second portion 434 of the menu 412 (e.g., ordering a size, large, medium, or tall). FIG. 5C, for a third period of time, illustrates user 25 standing in front of and looking at the third portion 436 of the menu 412 (e.g., ordering with whole milk, half & half, or soy milk).

In the example illustrated in FIG. 5A, the electronic device 10 provides a view 515A that enables user 25 to view a representation 552 of the first portion 432 of the menu 412 within a 3D environment 512A. In particular, FIG. 5A illustrates a scenario where the representation 552 includes embedded selectable interactable elements within the text, as illustrated by the underline (e.g., such as hyperlinks) that the user 25 may select based on the obtained physiological data. For example, interactable element 520 to select "Coffee", interactable element 522 to select "Tea", and interactable element 524 to select "Espresso". Additionally, FIG. 5A illustrates that the user has selected interactable element 520 ("Coffee") based on the indication area 525. In some implementations, indication area 525 is within view 515A, such that the selected interactable element 520 is presented so the user 25 knows they have selected that particular item as a part of an order. For example, if the user 25 focuses on the interactable element 520 for a particular period of time (e.g., two or more seconds), then the indication area 525 may flash to indicate to the user 25 they are about to make that selection. Then, after an additional time period (e.g., two or more seconds), then the indication area 525 may be highlighted or become a solid circle to indicate to the user 25 that they selected "Coffee" for their type of drink.

In the example illustrated in FIG. 5B, the electronic device 10 provides a view 515B that enables user 25 to view a representation 554 of the second portion 434 of the menu 412 within a 3D environment 512B. In particular, FIG. 5B illustrates a scenario where the representation 554 includes embedded selectable interactable elements proximate to a location of the text that the user 25 may select based on the obtained physiological data. For example, interactable element 530 is proximate to the potential selection "Large", interactable element 532 is proximate to the potential selection "Medium", and interactable element 534 is proximate to the potential selection "Small". Additionally, FIG. 5B illustrates that the user has selected interactable element 532 ("Medium") based on the indication area 535. In some implementations, indication area 535 is within view 515B, such that the indication area 535 is presented so the user 25 knows they have selected that particular item as a part of an order. For example, if the user 25 focuses on the interactable element 532 for a particular period of time (e.g., two or more seconds), then the indication area 535 may flash to indicate to the user 25 they are about to make that selection. Then, after an additional time period (e.g., two or more seconds), then the indication area 535 may be highlighted or become a solid circle to indicate to the user 25 that they selected "medium" as their size.

In the example illustrated in FIG. 5C, the electronic device 10 provides a view 515C that enables user 25 to view a representation 556 of the third portion 436 of the menu 412 within a 3D environment 512C. In particular, FIG. 5C illustrates a scenario where the user verbally selects a menu option as represented by speaking bubble 502 (e.g., " . . . with soy milk please."). The view 515C displays to the user 25 that they have selected "soy milk" as a menu option based on the indication area 545. In some implementations, indication area 545 is within view 515C, such that the indication area 545 is presented so the user 25 knows they have selected that particular item as a part of an order (e.g., visual confirmation of the audible order).

In some implementations, the content in each 3D environment 512 may entirely occupy the field of view for the user 25 (e.g., a fully immersive experience while wearing an HMD). For example, view 515 may include content (e.g., images, video, 3D reconstructions, or the like) from physical environment 400 captured by electronic device. In this example, view 515 may not include a view of physical environment 400 (e.g., via pass-through video captured by electronic device 10 or as seen through a transparent/translucent display). Alternatively, in some implementations, the content in each 3D environment 512 may only occupy a portion of the entire field of view for the user 25. For example, view 515 may include content (e.g., images, video, 3D reconstructions, or the like) from physical environment 400.

Figure 6B:
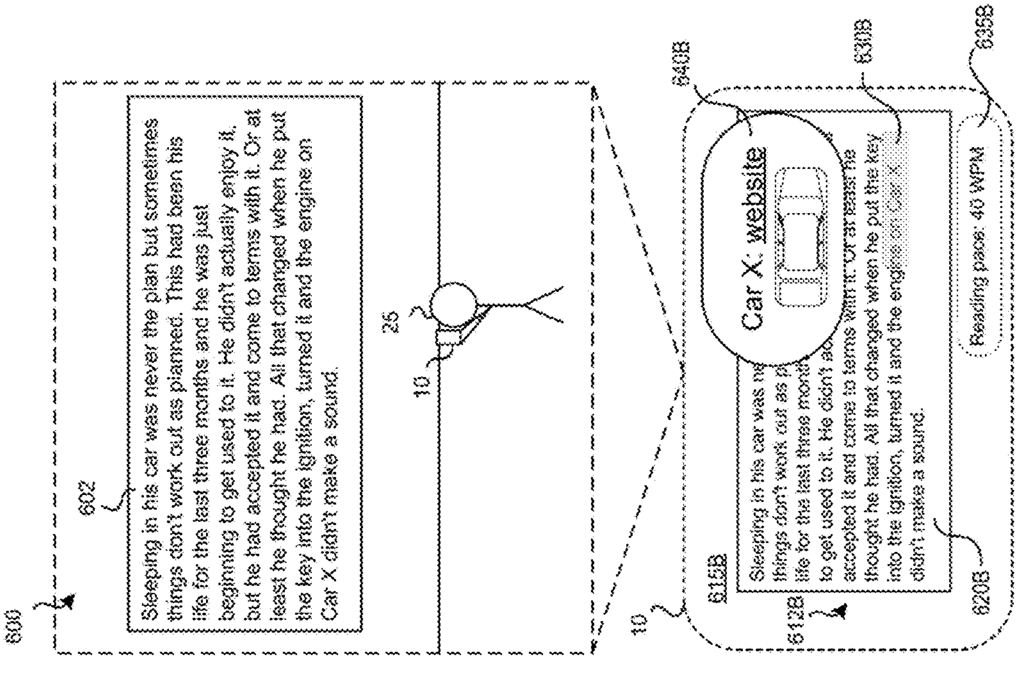
FIGS. 6A, 6B illustrate exemplary views of an electronic device during a reading of text, in accordance with some implementations.
Figure 6A:
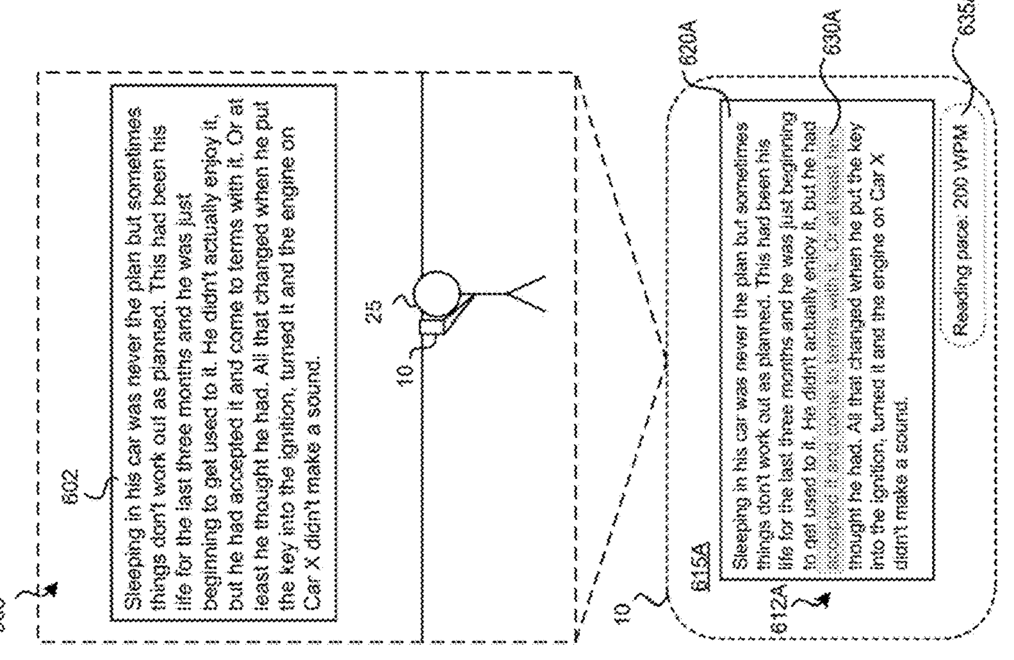

FIGS. 6A, 6B illustrate exemplary views of an electronic device during a reading of text, in accordance with some implementations. In some implementations, each view is of an XR environment that includes a representation of at least a portion of the physical environment, such as a user 25 reading an excerpt of a text block, in accordance with some implementations. For instance, FIGS. 6A, 6B illustrate an exemplary electronic device 10 providing view 615A of 3D environment 612A and view 615B of 3D environment 612B, respectively, operating in the physical environment 600 during a viewing of content (e.g., reading text 602 such as on a wall or from a book). For example, FIGS. 6A, 6B represent a user reading at two different periods of time while the user reads the text 602 in the physical environment or reads from the display 615 of the device 10.

In the example illustrated in FIG. 5A, the electronic device 10 provides a view 615A that enables user 25 to view a representation 620A of text 602 within a 3D environment 612A. In particular, FIG. 6A, for a first period of time, illustrates user 25 reading (e.g., focusing on, such as eye gaze and head movement) the text 602 at normal reading pace. For example, the device 10 may track a user's reading pace based on his or her eye gaze, and the device 10 may display a highlighted portion 630A on the view 615A as the user is reading the text 602. Additionally, FIG. 6A illustrates that the device 10 may display the user's current reading pace in the read pace element 635A. Alternatively, the reading pace is not presented on the view 615A, but is being tracked as described herein.

In the example illustrated in FIG. 6B, the electronic device 10 provides a view 615B that enables user 25 to view a representation 620B of the text 602 within a 3D environment 612B. In particular, FIG. 6B, for a second period of time, illustrates user 25 reading a portion of the text 602 at a slower reading pace (e.g., curious on a particular term or phrase, and may want to engage the selection (if it is a hyperlink) or generate a key word search of the term). For example, the device 10 may track a user's reading pace based on his or her eye gaze, and the device 10 may display a highlighted portion 630B on the view 615B as the user is reading the text 602. FIG. 6B further illustrates that the device 10 may display the user's current reading pace in the read pace element 635B. Alternatively, the reading pace is not presented on the view 615A but is being tracked as described herein. Additionally, FIG. 6B illustrates that user may be focused on the portion of the text 602 for the words: "Car X". In response, the view 615B presents an interaction element 640B to the user. The interaction element 640B, as illustrated in FIG. 6B, provides the user with a knowledge panel window based on a keyword search for the selected text excerpt (e.g., the word(s) that the system detects that the user is focused on). Alternatively, if the reader is reading the representation 620B of the text 602 from the view 615B (e.g., reading a virtual book), the representation 620B of the text 602 may include selectable text, such as hyperlinks. For example, when the user focuses his or her gaze on the hyperlinks, then a particular action may occur (e.g., providing the user with the website associated with the hyperlink), as described herein (e.g., placing an order on a menu as discussed with FIG. 5).

In some implementations, the content in each 3D environment 612 may entirely occupy the field of view for the user 25 (e.g., a fully immersive experience while wearing an HMD). For example, view 615 may include content (e.g., images, video, 3D reconstructions, or the like) from physical environment 600 captured by electronic device. In this example, view 615 may not include a view of physical environment 600 (e.g., via pass-through video captured by electronic device 10 or as seen through a transparent/translucent display). Alternatively, in some implementations, the content in each 3D environment 612 may only occupy a portion of the entire field of view for the user 25. For example, view 615 may include content (e.g., images, video, 3D reconstructions, or the like) from physical environment 600.

In the examples of FIGS. 1-6, the electronic device 10 is illustrated as a hand-held device. The electronic devices 10 may be a mobile phone, a tablet, a laptop, and so forth. In some implementations the device 10 is a laptop computer or a desktop computer. In some implementations, the device 10 has a touchpad and, in some implementations, the device 10 has a touch-sensitive display (also known as a "touch screen" or "touch screen display"). In some implementations, electronic device 10 may be worn by a user. For example, electronic devices 10 may be a watch, a head-mounted device (HMD), head-worn device (glasses), headphones, an ear mounted device, and so forth. In some implementations, functions of the device 10 is accomplished via two or more devices, for example, a mobile device and base station or a head mounted device and an ear mounted device. Various capabilities may be distributed amongst multiple devices, including, but not limited to, power capabilities, CPU capabilities, GPU capabilities, storage capabilities, memory capabilities, visual content display capabilities, audio content production capabilities, and the like. The multiple devices that may be used to accomplish the functions of electronic device 10 may communicate with one another via wired or wireless communications and/or via an intermediary device such as a playback session server.

In some implementations, the electronic device 10 includes a position tracking instruction set to track a position of a viewer/reader (e.g., user 25) relative to a 3D environment. This may involve tracking a position or movement of the viewer in a physical environment (e.g., physical environment 5), virtual environment, or XR environment. Position, including 2D or 3D coordinate information or orientation, may be tracked based on information from I/O device(s) and sensor(s) or image sensor system(s). In some implementations, the position tracking instruction set is executed to evaluate images of a physical environment, recognize objects in the physical environment, and determine a viewer position relative to the objects in the physical environment. In some implementations, the viewer position is additionally or alternatively tracked using an inertial measurement unit (IMU), an accelerometer, a magnetometer, or a gyroscope. In some implementations, a visual inertial odometry (VIO) technique or a simultaneous localization and mapping (SLAM) technique is applied to track viewer position. In some implementations, the position tracking instruction set implements a machine learning model that uses image data or sensor data to track viewer position.

Figure 7:
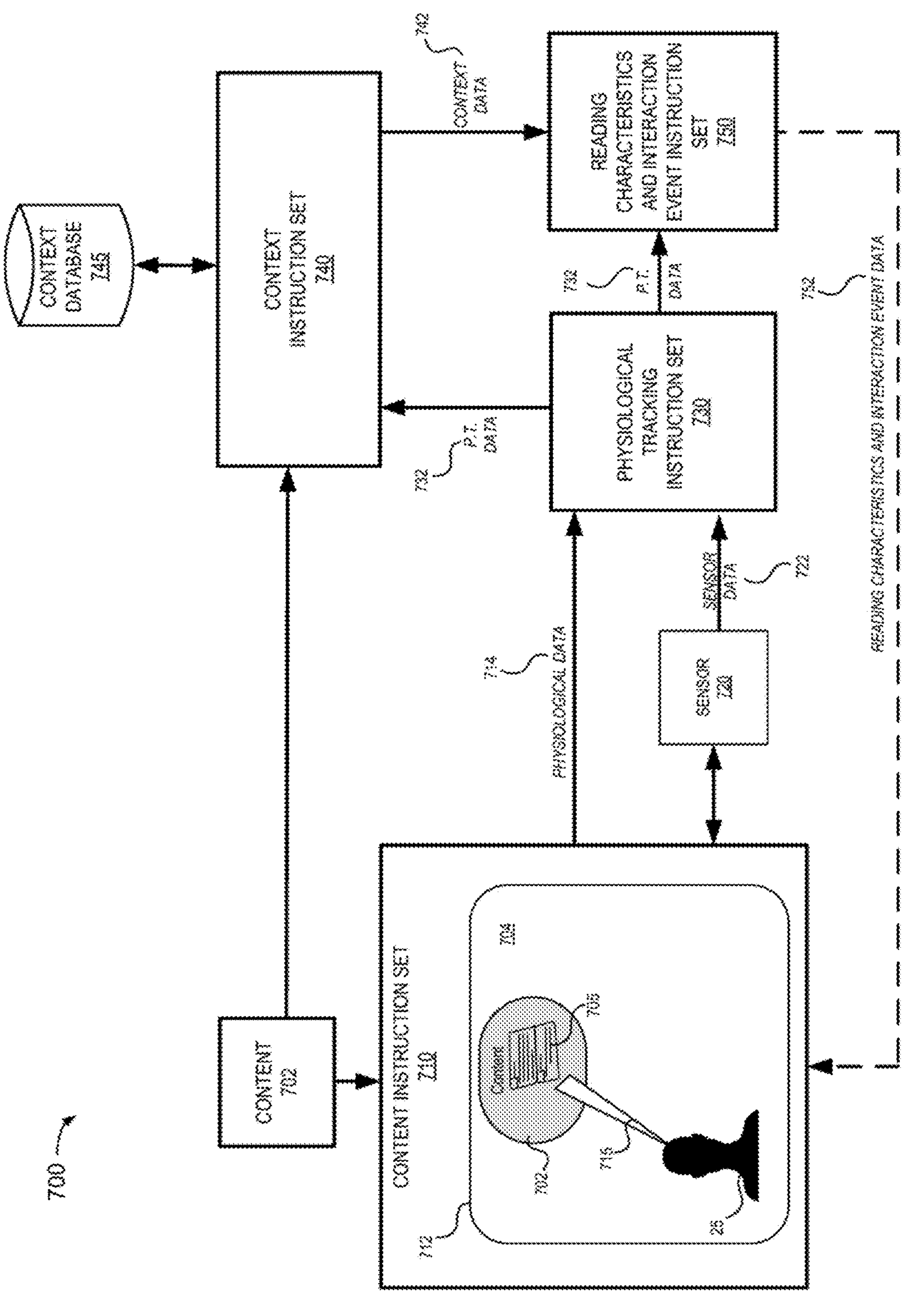
FIG. 7 illustrates a system diagram for detecting an interaction event of the user viewing content based on physiological data and reading characteristic assessments in accordance with some implementations.

FIG. 7 is a system flow diagram of an example environment 700 in which an interaction event assessment system can assess an interaction event of a user based on physiological data and associated reading characteristics of the user according to some implementations. In some implementations, the system flow of the example environment 700 is performed on a device (e.g., device 10 of FIG. 1), such as a mobile device, desktop, laptop, or server device. The content of the example environment 700 can be displayed on a device (e.g., device 10 of FIG. 1) that has a screen (e.g., display 15) for displaying images and/or a screen for viewing stereoscopic images such as an HMD. In some implementations, the system flow of the example environment 700 is performed on processing logic, including hardware, firmware, software, or a combination thereof. In some implementations, the system flow of the example environment 700 is performed on a processor executing code stored in a non-transitory computer-readable medium (e.g., a memory).

The system flow of the example environment 700 acquires and presents content (e.g., text, or an image/video that includes at least a portion of text) to user 25, analyzes the content and/or the environment for context data, obtains physiological data associated with the user during presentation of the content, assesses a user's intent to interact with a portion of the text (e.g., interactable element 705) based on the physiological data of the user and updates the content based on the interaction event (e.g., if the user 25 focuses on the interactable element 705 for a certain period of time to activate or select the interactable element 705). For example, an interaction event assessment technique described herein determines, based on obtained physiological data, the user's intent to interact with a portion of the text (e.g., interactable element 705) during an experience (e.g., watching a video) by updating the content that is based on the interaction event of the user (e.g., a notification, auditory signal, an alert, and the like, that alerts the user that they have selected the interactable element 705 during the presentation of content 702).

The example environment 700 includes a content instruction set 710 that is configured with instructions executable by a processor to provide and/or track content 702 for display on a device (e.g., device 10 of FIG. 1). For example, the content instruction set 710 provides content presentation instant 712 that includes content 702 to a user 25 while user is within a physical environment 704 (e.g., a room, outside, etc.). For example, content 702 may include background image(s) and sound data (e.g., a video). The content presentation instant 712 could be an XR experience that includes some virtual content and some images or views of a physical environment. Alternatively, the user could be wearing a HMD and is looking at a real physical environment either via a live camera view, or the HMD allows a user to look through the display, such as wearing smart glasses that user can see through, but still be presented with visual and/or audio cues. During an experience, while a user 25 is viewing the content 702, pupillary data 715 (e.g., pupillary data 40 such as eye gaze characteristic data) of the user's eyes can be monitored and sent as physiological data 714. Additionally, other physiological data can be monitored and sent as physiological data 714 such as head movement data obtained from an IMU or image data.

The environment 700 further includes a physiological tracking instruction set 730 to track a user's physiological attributes as physiological tracking data 732 using one or more of the techniques discussed herein or as otherwise may be appropriate. For example, the physiological tracking instruction set 730 may acquire physiological data 714 (e.g., pupillary data 715) from the user 25 viewing the content 702. Additionally, or alternatively, a user 25 may be wearing a sensor 720 (e.g., such as an EEG sensor, an EDA sensor, heart rate sensor, etc.) that generates sensor data 722 (e.g., IMU or pose data, EEG data, EDA data, heart rate data, and the like) as additional physiological data. Thus, as the content 702 is presented to the user as content presentation instant 712, the physiological data 714 (e.g., pupillary data 715) and/or sensor data 722 is sent to the physiological tracking instruction set 730 to track a user's physiological attributes as physiological tracking data 732, using one or more of the techniques discussed herein or as otherwise may be appropriate.

In an example implementation, the environment 700 further includes a context instruction set 740 that is configured with instructions executable by a processor to obtain the experience data presented to the user (e.g., content 702) and other sensor data (e.g., image data of the environment 704, the user's 25 face and/or eye's, etc.), and generate context data 742 (e.g., identifying people, objects, etc. of the content 702 and the environment 704). For example, the context instruction set 740 acquires content 702 and sensor data 722 (e.g., image data) from the sensor 720 (e.g., an RGB camera, a depth camera, etc.) and determines context data 742 based on identifying areas of the content while the user is viewing the presentation of the content 702 (e.g., a first time viewed content/video). Alternatively, the context instruction set 740 selects context data associated with content 702 from a context database 745 (e.g., if the content 702 was previously analyzed by the context instruction set, e.g., a previously viewed/analyzed video). In some implementations, the context instruction set 740 generates a scene understanding associated with content 702 and/or environment 704 as the context data 742. For example, the scene understanding can be utilized to track the overall context of what the user may be focused on during the presentation of content 702, or where the user is, what the user is doing, what physical objects or people are in the vicinity of the user with respect to the environment 704.

In an example implementation, the environment 700 further includes reading characteristics and interaction event instruction set 750 that is configured with instructions executable by a processor to assess the user's 25 intent to interact with (e.g., select) the interactable element 705 (e.g., a portion of the text) based on a physiological response (e.g., eye gaze response via pupillary data 715) using one or more of the techniques discussed herein or as otherwise may be appropriate. For example, intent of the user 25 to interact with the interactable element 705 that may be assessed such as determining that the user 25 is focused on a particular illuminated region of the interactable element 705 (e.g., such as interactable element 303 of FIG. 3B). In particular, the reading characteristics and interaction event instruction set 750 acquires physiological tracking data 732 from the physiological tracking instruction set 730 and determines the intent of the user 25 to interact with (select) the interactable element 705 during the presentation of the content 702 while the user is viewing content 702 (e.g., reading text with embedded selectable elements). In some implementations, the reading characteristics and interaction event instruction set 750 can then provide reading characteristics and interaction event data 752 (e.g., data that signals that the user selected the interactable element 705 and reading characteristics associated with the user 25 while viewing the content 702) to the content instruction set 710 based on the interaction event assessment.

In some implementations, the reading characteristics and interaction event instruction set 750 also acquires context data 742 from the context instruction set 740 (e.g., scene understanding data) with the physiological tracking data 732 to determine the intent of the user 25 to interact with (select) the interactable element 705 during the presentation of the content 702. For example, the context data 742 may provide a scene analysis that can be used by the reading characteristics and interaction event instruction set 750 to understand what the person is looking at, where they are at, etc., and improve the determination of the intent of the user to select the interactable element 705.

Figure 8:
FIG. 8 is a flowchart representation of a method for determining whether to initiate an interaction event during the presentation of the content based on determining whether the user is reading text or intends an interaction with a portion of the text in accordance with some implementations.
Figure 8:
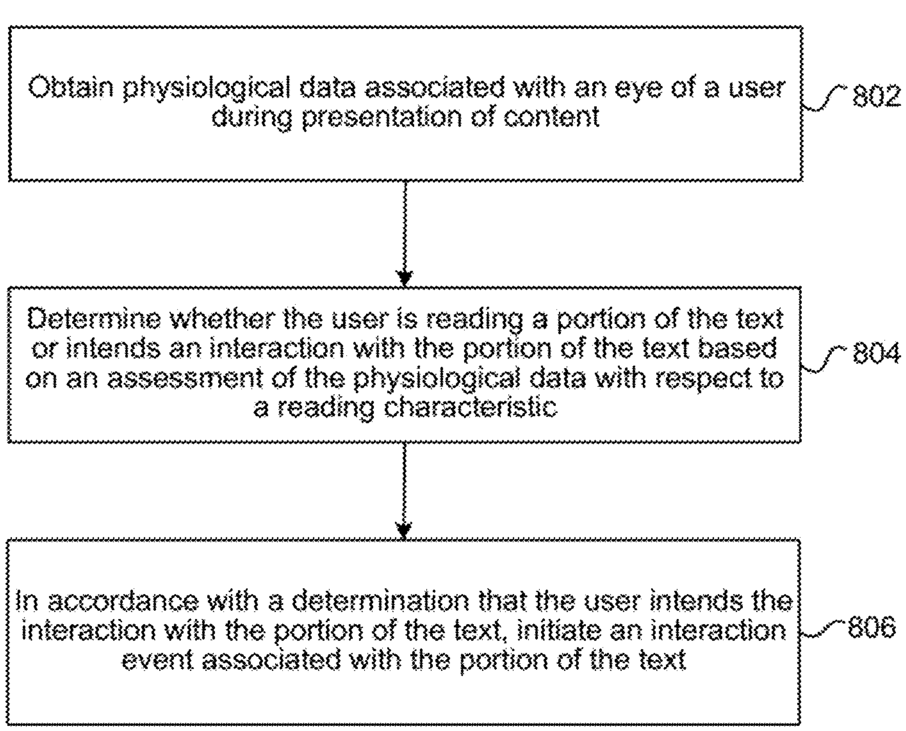

FIG. 8 is a flowchart illustrating an exemplary method 800. In some implementations, a device such as device 10 (FIG. 1) performs the techniques of method 800 to determine whether to initiate an interaction event during the presentation of the content based on determining whether the user is reading text or intends an interaction with a portion of the text. For example, the method 800 may identify that, during a particular segment of an experience, the user's gaze characteristics (e.g., pupil dilation vs. constriction, stable gaze direction, and/or velocity of pupil movements) corresponds to a user focusing on a portion of text such as a particular icon or an interactable element (referred to herein as an "interactive element"). For example, a user may direct their attention to a portion of text to initiate a "click" or other interaction. This can be used as a user interface selection tool, device wake-up signal, etc., and might be combined with other eye or touch-based mechanisms to improve SNR, robustness, and response time.

In some implementations, the techniques of method 800 are performed on a mobile device, desktop, laptop, HMD, or server device. In some implementations, the method 800 is performed on processing logic, including hardware, firmware, software, or a combination thereof. In some implementations, the method 800 is performed on a processor executing code stored in a non-transitory computer-readable medium (e.g., a memory).

At block 802, the method 800 obtains physiological data associated with an eye of a user during presentation of content, and the content includes text. For example, as illustrated in FIG. 5A, the user 25 selected "coffee" by focusing his or her gaze on the interactable element 520 (e.g., the actual text on the menu is selectable), as indicated by the selection notification of the indication area 525. Additionally, or alternatively, the interactable element may be positioned proximate to the text (e.g., a separate selectable element). For example, as illustrated in FIG. 5B, the user 25 selected "medium" by focusing his or her gaze on the interactable element 532, as indicated by the selection notification of the indication area 535.

In some implementations, obtaining physiological data includes EEG amplitude/frequency, pupil modulation, eye gaze saccades, head movements, and the like, from which pupil response/gaze direction/movement can be determined. In some implementations, obtaining physiological data (e.g., pupillary data 40) is associated with a gaze of a user that may involve obtaining images of the eye or electrooculography signal (EOG) data from which gaze direction and/or movement can be determined. In some implementations, the physiological data includes at least one of skin temperature, respiration, photoplethysmogram (PPG), electrodermal activity (EDA), eye gaze tracking, and pupillary movement that is associated with the user. In some implementations, obtaining physiological data includes head movements of the user (e.g., obtained from an IMU or from image sensor data), such as head movement data 316.

In some implementations, determining the movement and/or the location and features of the head 27 of the user 25 (e.g., an edge of the eye, a nose or a nostril) are extracted by the device 10 and used in finding coarse location coordinates of the eyes 45 of the user 25, thus simplifying the determination of precise eye 45 features (e.g., position, gaze direction, etc.) and making the gaze characteristic(s) measurement and corresponding reading characteristics more reliable and robust. Furthermore, the device 10 may readily combine the 3D location of parts of the head 27 with gaze angle information obtained via eye part image analysis in order to identify a given on-screen object at which the user 25 is looking at any given time. In some implementations, the use of 3D mapping in conjunction with gaze tracking allows the user 25 to move his or her head 27 and eyes 45 freely while reducing or eliminating the need to actively track the head 27 using sensors or emitters on the head 27.

By tracking the eyes 45, some implementations reduce the need to re-calibrate the user 25 after the user 25 moves his or her head 27. In some implementations, the device 10 uses depth information to track the pupil's 50 movement, thereby enabling a reliable present pupil diameter to be calculated based on a single calibration of user 25. Utilizing techniques such as pupil-center-corneal reflection (PCCR), pupil tracking, and pupil shape, the device 10 may calculate the pupil diameter, as well as a gaze angle of the eye 45 from a fixed point of the head 27, and use the location information of the head 27 in order to re-calculate the gaze angle and other gaze characteristic(s) measurements. In addition to reduced recalibrations, further benefits of tracking the head 27 may include reducing the number of light projecting sources and reducing the number of cameras used to track the eye 45.

Some implementations obtain physiological data and other user information to help improve a user experience. In such processes, user preferences and privacy should be respected, as examples, by ensuring the user understands and consents to the use of user data, understands what types of user data are used, has control over the collection and use of user data and limiting distribution of user data, for example, by ensuring that user data is processed locally on the user's device. Users should have the option to opt in or out with respect to whether their user data is obtained or used or to otherwise turn on and off any features that obtain or use user information. Moreover, each user will have the ability to access and otherwise find out anything that the system has collected or determined about him or her. User data is stored securely on the user's device. User data that is used as input to a machine learning model is stored securely on the user's device, for example, to ensure the user's privacy. The user's device may have a secure storage area, e.g., a secure enclave, for securing certain user information, e.g., data from image and other sensors that is used for face identification or biometric identification. The user data associated with the user's body and/or attentive state may be stored in such a secure enclave, restricting access to the user data and restricting transmission of the user data to other devices to ensure that user data is kept securely on the user's device. User data may be prohibited from leaving the user's device and may be used only in machine learning models and other processes on the user's device.

At block 804, the method 800 determines whether the user is reading a portion of the text or intends an interaction with the portion of the text based on an assessment of the physiological data with respect to a reading characteristic.

In some implementations, determining whether the user is reading the text or intends an interaction with the portion of the text may be based on determining whether the user is reading, the user's reading pace, and/or whether the user is focused on a particular element and for how long, and the like, or a combination thereof. For example, this may involve detecting that the user is transitioning from reading to interacting or the user is immediately interacting instead of reading. In some implementations, algorithms or machine learning models may be configured/refined based on (e.g., learning from) user specific actions. For example, user actions may include the user's actual reading pace, the user's actual/confirmed transitions from reading to interaction, or the user's canceling of auto-triggered interactions (e.g., indicating a false activation). Additionally, user actions may include a user's negative response to an auto-triggered interaction, such as eye twitch, eye closing, and/or squinting (e.g., indicating a false activation).

In some implementations, the method 800 assesses the physiological data with respect to a reading characteristic. In some implementations, the system may determine whether the user's gaze may be moving in a way that corresponds to reading. In some implementations, the system may determine whether the user's gaze movement corresponds to an average reading pace and/or the user's specific reading pace. In some implementations, the pupillary response is a direction of the pupillary response, a velocity of the pupillary response, or pupillary fixations (e.g., derived from eye gaze dynamics and saccade characteristics). In some implementations, the pupillary response is derived from a saccade characteristic (e.g., microsaccades and saccadic intrusions). In some implementations, saccade characteristics are a separate attribute or type of physiological data than the pupillary response, such that the method 800 may alternatively, at block 804, determine a saccade characteristic other than a pupillary response during the presentation of the interaction element. For example, saccade characteristics may include measuring microsaccades and/or saccadic intrusions.

In some implementations, determining whether the user is reading the portion of the text or intends an interaction with the portion of the text based on the assessment includes determining a transition detection from the user reading the text to the interaction event with the portion of the text. In some implementations, determining whether the user is reading the text or intends an interaction with the portion of the text based on the assessment includes determining a reading pace of the user from the user reading the text, and comparing the reading pace to a threshold.

In some implementations, determining whether the user is reading the text or intends an interaction with the portion of the text based on the assessment includes detecting that the user is transitioning from reading the text to interacting with the portion of the text. For example, detecting the user transitioning from reading to interacting or the user immediately interacting instead of reading.

At block 806, the method 800, in accordance with a determination that the user intends the interaction with the portion of the text, initiates an interaction event associated with the portion of the text. In some implementations, the interaction event may be embedded within a portion of the text. For example, as illustrated in FIG. 5A, the user 25 places an order for a coffee based on the system determining the user focused his or her attention on the interactable element 520 (e.g., the phrase/word "coffee"). Additionally, for example, as illustrated in FIG. 6B, the user 25 slows his or her reading pace and focuses on a phrase (e.g., "Car X"), and the system provides interaction element 640B, which provides the user with a knowledge panel window based on a keyword search for the selected text excerpt (e.g., the word(s) that the system detects that the user is focused on). In some implementations, the method 800, in accordance with a determination that the user is reading the portion of the text, forgoes initiating the interaction event associated with the portion of the text. For example, the user increases his or her reading pace after being distracted, or is no longer interested in the portion of the text (e.g., does not want to be presented a knowledge panel related to "Car X").

In some implementations, the method 800 may cancel the interaction event based on determining that the interaction event includes a false positive activation based on a detection of an abnormal user action. In some implementations, the abnormal user action is an eye twitch, an eye closing, or an eye squinting. For example, the system may determine that the user's gaze characteristics includes an eye twitch, eye closing, and/or squinting. Thus, based on those type of gaze characteristics (e.g., false positives), then an interaction event may be cancelled (e.g., a selection notification may be removed).

In some implementations, a machine learning algorithm may be determined based predicting a "click" or "no click" for each time point based on the presence of an attention-induced pupil response (e.g., based on the presence of an attention-induced pupil response with respect to the text, and refinement thereof). In an exemplary embodiment, determining whether the user is reading a portion of the text or intends an interaction with the portion of the text based on an assessment includes determining scene-induced pupil response variation characteristics for the portion of the text, and determining the interaction event of the user during the presentation of content based on the scene-induced pupil response variation characteristics for the portion of the text. For example, when a user's gaze intersects with a portion of the text (e.g., interaction element 303 of FIG. 3A), a machine learning protocol can predict a "click" or "no click" for each time point, based on the presence of an attention-induced pupil response. Therefore, in some implementations, the interaction event may be classified using a machine learning technique based on the pupillary response for the interaction element and the user's associated reading characteristics (e.g., a machine learning "click" model). In some implementations, the machine learning technique is refined based on at least one of a reading pace of the user, a detected transition from reading the text to an intent to interact with the portion of the text, and a detected intent of the user to cancel an interaction event.

In some implementations, determining the pupillary response and associated reading characteristics during the presentation of the interaction element may be based on determining a variability of the pupillary response to a threshold (e.g., a reading pace). An example threshold limit for the variability of the pupillary response may be based on a machine learning model output. For example, if the machine learning model takes the physiological data as input and outputs a probability of click intent (e.g., 70%), then a determination may be made that any pupil response causing a probability under 70% is no click, while a pupil response leading to a machine learning model output at or above 70% is a click.

Another type of threshold could be an outlier detection, e.g., if the pupillary response or other physiological data changes beyond an accepted range, and that data may be rejected and considered as noise. Likewise, if response changes are so small that the system would have low confidence in measuring such a small change, the system might also reject that data as noise.

In some implementations, determining whether to initiate an interaction event includes determining scene-induced pupil response variation characteristics for the interaction element, and determining the interaction event of the user during the presentation of the interaction element based on the scene-induced pupil response variation characteristics of the interaction element and/or reading characteristics of the user. A method may include subtracting from the pupil response the low-level scene-induced pupil response variation as given by the reading characteristics via a machine learning model. For example, when a user's gaze intersects with a portion of the text (e.g., indication area 535 of interaction element 532 of FIG. 5B), a machine learning algorithm predicts "click" or "no click" for each time point, based on the presence of an attention-induced pupil response (e.g., based on the presence of an attention-induced pupil response with respect to the text).

In some implementations, the techniques described herein can utilize a training or calibration sequence to adapt to the specific physiological characteristics of a particular user 25. In some implementations, the techniques present the user 25 with a training scenario in which the user 25 is instructed to interact (e.g., focus) with some particular text (e.g., interactive text). For example, as discussed herein with reference to FIG. 4, the notification 460 may provide the user instructions to focus on particular portions of the menu to train a machine learning algorithm. For example, the notification 460 may instruct the user to focus on the word "Coffee" in the representation 442 of the first portion 432 for three seconds, then focus on the word "Medium" in the representation 444 of the second portion 434 for three seconds, and finally focus on the word "Soy Milk" in the representation 446 of the third portion 436 for three seconds. By providing the user 25 with a known intent or area of interest (e.g., via instructions), the techniques can record the user's physiological data (e.g., pupillary data 40) and identify a pattern associated with the user's physiological data.

In some implementations, the method 800 includes adjusting content in response to initiating the interaction event. (e.g., a user "clicks" on the interactable element). For example, the techniques can change a visual characteristic 30 (e.g., a feedback mechanism) associated with content 20 in order to further adapt to the unique physiological characteristics of the user 25 (e.g., reading pace). For example, the techniques can direct a user to read a particular phrase (e.g., a phrase that contains an interactive element) associated with an identified area in the center of the screen on the count of three and record the user's physiological data (e.g., pupillary data 40) to identify a pattern associated with the user's interaction event (e.g., reading characteristics). Moreover, the techniques can change or alter the text in order to identify a pattern associated with the user's physiological response to the altered text. In some implementations, the pattern associated with the physiological response of the user 25 is stored in a user profile associated with the user and the user profile can be updated or recalibrated at any time in the future (e.g., storing a reading pace for each user). For example, the user profile could automatically be modified over time during a user experience to provide a more personalized user experience (e.g., a personal educational experience for optimal learning experience while studying). In some implementations, a "click" threshold may be utilized for training a machine learning model. For example, a "click" threshold may be increased or decreased in real-time to maximize true positive events and minimize false positives. Additionally, or alternatively, in some implementations, implicit feedback from the user (e.g., if a sequence of interactions indicates one interaction was an error) may be used to determine true versus false positives in real-time and the "click" threshold may be adapted by the system accordingly. In some implementations, the techniques described herein can utilize a training process or calibration sequence to involve "gamification", where the user learns to achieve a certain task over time where there is an animation that corresponds to the real-time output of a machine learning model prediction about the probability of click. For example, controlling and closing a ring animation, where the ring closes in proportion to the model's predicated click probability.

In some implementations, the machine learning model is a neural network (e.g., an artificial neural network), decision tree, support vector machine, Bayesian network, or the like. These labels may be collected from the user beforehand, or from a population of people beforehand, and fine-tuned later on for individual users. Creating this labeled data may require many users going through an experience (e.g., a meditation experience) where the users listen to natural sounds with intermixed natural-probes (e.g., an auditory stimulus) and then randomly are asked how focused or relaxed they were (e.g., interaction event) shortly after a probe was presented. The answers to these questions can generate a label for the time prior to the question and a deep neural network or deep long short term memory (LSTM) network might learn a combination of features specific to that user or task given those labels (e.g., low interaction event, high interaction event, etc.).

In some implementations, the method 800 further includes adjusting content in response to determining an intent of the interaction with a portion of the text. For example, as illustrated in the system flow diagram of environment 700 of FIG. 7, when it is determined that user's intent is to "click" (e.g., interact/focus) on the portion of the text (e.g., interactable element 705), the reading characteristics and interaction event instruction set 750 provides reading characteristics and interaction event data 752 to the content instruction set 710 to update the content (e.g., change the content based on the selection of the icon—interactable element 705).

In some implementations, the techniques described herein obtain physiological data (e.g., pupillary data 40, EEG amplitude/frequency data, pupil modulation, eye gaze saccades, head movements, etc.) and associated reading characteristics from the user based on identifying typical interactions of the user with the experience. For example, the techniques may determine that a variability of an eye gaze characteristic of the user correlates with an interaction with the experience. Additionally, the techniques described herein may then adjust a visual characteristic of the experience, or adjust/change a sound associated with the interaction element, to enhance physiological data associated with future interactions with the experience and/or the interaction element presented within the experience. Moreover, in some implementations, changing an interaction element after the user interacts with the experience informs the physiological response of the user in subsequent interactions with the interaction element or a particular segment of the experience. For example, the user may present an anticipatory physiological response associated with the change within the interaction element (e.g., a change in reading pace of the interaction element). Thus, in some implementations, the technique identifies an intent of the user to interact with the interaction element based on an anticipatory physiological response. For example, the technique may adapt or train an instruction set by capturing or storing physiological data of the user based on the interaction of the user with the experience (e.g., reading pace), and may detect a future intention of the user to interact with the experience by identifying a physiological response of the user in anticipation of the presentation of the enhanced/updated interaction element.

In some aspects, the method 800 determines a context of the experience based on sensor data of the environment. For example, determining a context may involve using computer vision to generate a scene understanding of the visual and/or auditory attributes of the environment—where is the user, what is the user doing, what objects are nearby. Additionally, a scene understanding of the content presented to the user could be generated that includes the visual and/or auditory attributes of what the user was watching.

In some aspects, different contexts of the content presented and the environment are analyzed to determine where the user is, what the user is doing, what objects or people are nearby in the environment or within the content, what the user did earlier (e.g., meditated in the morning). Additionally, context analysis may include image analysis (semantic segmentation), audio analysis (jarring sounds), location sensors (where user is), motion sensors (fast moving vehicle), and even access other user data (e.g., a user's calendar). In an exemplary implementation, the method 800 may further include determining the context of the experience by generating a scene understanding of the environment based on the sensor data of the environment, the scene understanding including visual or auditory attributes of the environment, and determining the context of the experience based on the scene understanding of the environment.

In some implementations, the sensor data includes image data, and generating the scene understanding is based at least on performing semantic segmentation of the image data and detecting one or more objects within the environment based on the semantic segmentation. In some implementations, determining the context of the experience includes determining an activity of the user based on the scene understanding of the environment. In some implementations, the sensor data includes location data of the user, and determining the context of the experience includes determining a location of the user within the environment based on the location data.

In some implementations, determining the context of the experience includes determining an activity of the user based on a user's schedule. For example, the system may access a user's calendar to determine if a particular event is occurring when the particular interaction event is assessed. For example, different applications may include different interaction elements to be provided to the user to select via his or her pupillary response (eye gaze characteristics) and reading characteristics.

In some implementations, customization of the experience could be controlled by the user. For example, a user could select the experience he or she desires, such as he or she can choose the ambience, background scene, music, etc. Additionally, the user could alter the threshold of selecting the interactive element. For example, the user can customize the sensitivity of triggering the interactive element based on prior experience of a session. For example, a user may desire to not have as many notifications and allow some mind wandering (e.g., eye position deviations) before an interactive element is triggered. Thus, particular experiences can be customized on triggering a threshold when higher criteria is met. For example, a user may have to look at a particular interactive element for longer (or shorter) than the previously discussed threshold of two seconds to toggle the interactive element (e.g., shakes or flashes) and/or a longer (or shorter) threshold of two seconds after the toggle to actually select the interactive element. For example, the user may want the threshold set at three seconds before interactive element is toggled, but only want one additional second (e.g., after the interactive element is toggled and begins to shake) before the interactive element is actually selected and thus the system performs the action of the interactable element being selected.

In some implementations, one or more pupillary, EEG, and/or reading characteristics may be determined, aggregated, and used to classify the user's intent to determine an interaction event occurrence using statistical or machine learning techniques. In some implementations, the physiological data is classified based on comparing the variability of the physiological data to a threshold.

In some implementations, the method 800 further includes adjusting content corresponding to the experience based on the interaction event (e.g., customized to the interaction event of the user) and the associated reading characteristics. For example, content recommendation for a content developer can be provided based on determining interaction events during the presented experience and changes of the experience or content presented therein. For example, the user may focus well when particular types of content are provided. In some implementations, the method 800 may further include identifying content based on similarity of the content to the experience, and providing a recommendation of the content to the user based on determining that the user has the a particular reading characteristic during the experience (e.g., focused on a particular text, phrase or icon compared to an average reading pace). In some implementations, the method 800 may further include customizing content included in the experience based on the interaction event and the associated reading characteristics of the user (e.g., breaking the content such as the selectable text into smaller and/or more distinct pieces).

In some implementations, an estimator or statistical learning method is used to better understand or make predictions about the physiological data (e.g., pupillary data characteristics, head movements, etc.) and associated reading characteristics. For example, statistics for pupillary data may be estimated by sampling a dataset with replacement data (e.g., a bootstrap method).

In some implementations, a machine learning model (e.g., a trained neural network) is applied to identify patterns in physiological data and the associated reading characteristics of the user, including identification of physiological responses to presentation of content (e.g., content 20 of FIG. 1) during a particular experience (e.g., education, meditation, instructional, etc.). Moreover, the machine learning model may be used to match the patterns with learned patterns corresponding to indications of interest or intent of the user 25 to interact with the interaction element, such as reading selectable text selections (e.g., ordering from a menu). In some implementations, the techniques described herein may learn patterns specific to the particular user 25. For example, the techniques may learn from determining that a peak pattern represents an indication of interest or intent of the user 25 in response to a particular visual characteristic 30 within the content and use this information to subsequently identify a similar peak pattern as another indication of interest or intent of the user 25 (e.g., a pattern in reading pace). Such learning can take into account the user's relative interactions with multiple visual characteristics 30, in order to further adjust the visual characteristic 30 and enhance the user's physiological response to the experience and the presented content (e.g., focusing on particular areas of content versus other distracting areas).

In some implementations, the techniques described herein can identify a particular object within the content presented on the display 15 of the device 10 at a position in the direction of the user's gaze. Moreover, the techniques can change a state of the visual characteristic 30 associated with the particular object or the overall content experience responsively to a spoken verbal command received from the user 25 in combination with the identified interaction event of the user 25. For example, a particular object within the content may be an icon associated with a software application, and the user 25 may gaze at the icon, say the word "select" to choose the application, and a highlighting effect may be applied to the icon. The techniques can then use further physiological data (e.g., pupillary data 40) in response to the visual characteristic 30 (e.g., an interactive element) to further identify an interaction event of the user 25 as a confirmation of the user's verbal command. In some implementations, the techniques can identify a given interactive item responsive to the direction of the user's gaze, and to manipulate the given interactive item responsively to physiological data (e.g., variability of the gaze characteristics). The techniques can then confirm the direction of the user's gaze based on further identifying interaction events of a user with physiological data in response to interactions with the experience (e.g., interacting within an intense video game). In some implementations, the techniques can remove an interactive item or object based on the identified interest or intent. In other implementations, the techniques can automatically capture images of the content at times when an interest or intent of the user 25 is determined.

Figure 9:
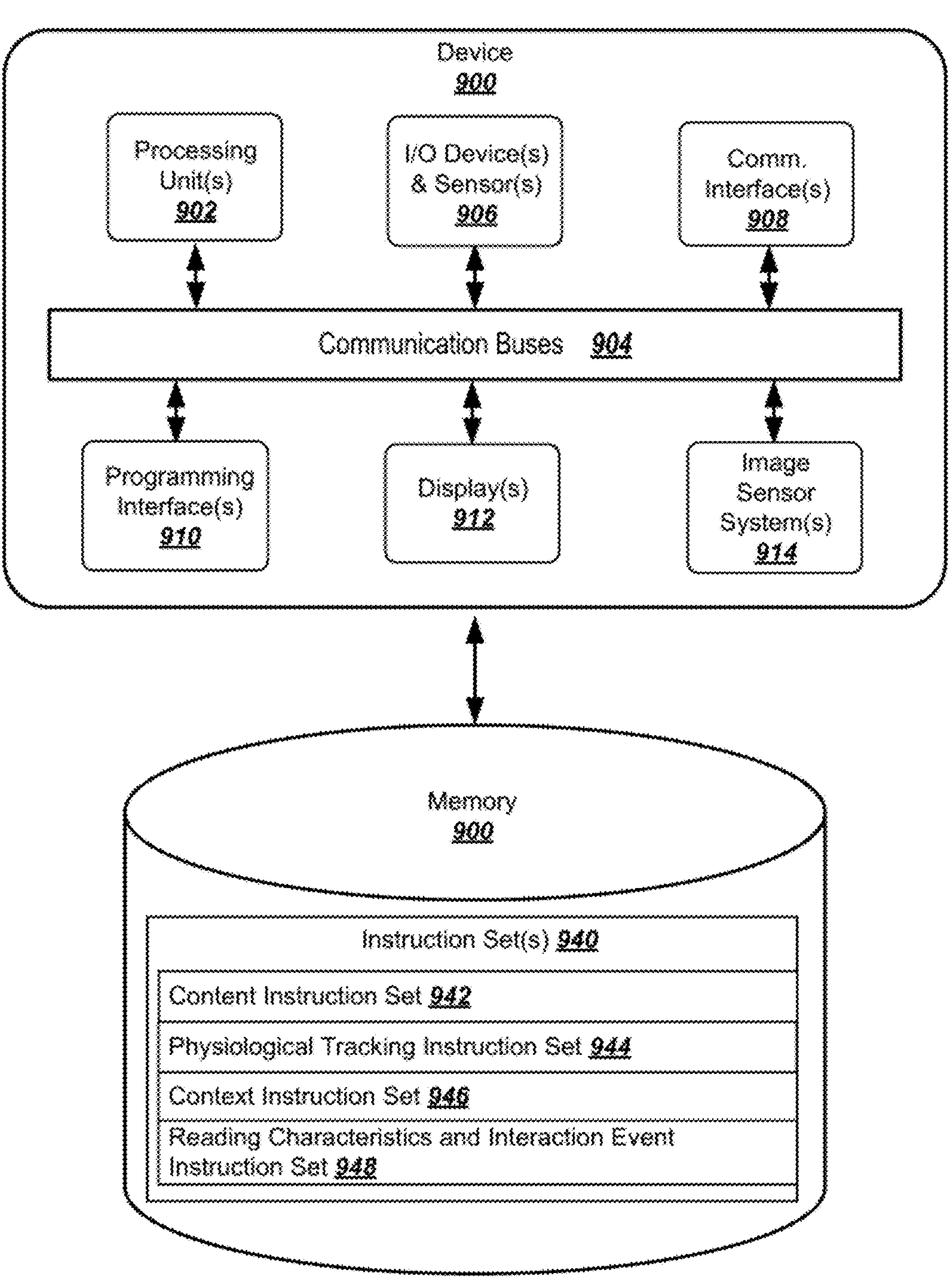
FIG. 9 illustrates device components of an exemplary device in accordance with some implementations.

FIG. 9 is a block diagram of an example device 900. Device 900 illustrates an exemplary device configuration for device 10. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 10 includes one or more processing units 902 (e.g., microprocessors, ASICs, FPGAs, GPUs, CPUs, processing cores, and/or the like), one or more input/output (I/O) devices and sensors 906, one or more communication interfaces 908 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, and/or the like type interface), one or more programming (e.g., I/O) interfaces 910, one or more displays 912, one or more interior and/or exterior facing image sensor systems 914, a memory 920, and one or more communication buses 904 for interconnecting these and various other components.

In some implementations, the one or more communication buses 904 include circuitry that interconnects and controls communications between system components. In some implementations, the one or more I/O devices and sensors 906 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some implementations, the one or more displays 912 are configured to present a view of a physical environment or a graphical environment to the user. In some implementations, the one or more displays 912 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), and/or the like display types. In some implementations, the one or more displays 912 correspond to diffractive, reflective, polarized, holographic, etc. waveguide displays. In one example, the device 10 includes a single display. In another example, the device 10 includes a display for each eye of the user.

In some implementations, the one or more image sensor systems 914 are configured to obtain image data that corresponds to at least a portion of the physical environment 5. For example, the one or more image sensor systems 914 include one or more RGB cameras (e.g., with a complimentary metal-oxide-semiconductor (CMOS) image sensor or a charge-coupled device (CCD) image sensor), monochrome cameras, IR cameras, depth cameras, event-based cameras, and/or the like. In various implementations, the one or more image sensor systems 914 further include illumination sources that emit light, such as a flash. In various implementations, the one or more image sensor systems 914 further include an on-camera image signal processor (ISP) configured to execute a plurality of processing operations on the image data.

The memory 920 includes high-speed random-access memory, such as DRAM, SRAM, DDR RAM, or other random-access solid-state memory devices. In some implementations, the memory 920 includes non-volatile memory, such as one or more magnetic disk storage devices, optical disk storage devices, flash memory devices, or other non-volatile solid-state storage devices. The memory 920 optionally includes one or more storage devices remotely located from the one or more processing units 902. The memory 920 includes a non-transitory computer readable storage medium.

In some implementations, the memory 920 or the non-transitory computer readable storage medium of the memory 920 stores an optional operating system 930 and one or more instruction set(s) 940. The operating system 930 includes procedures for handling various basic system services and for performing hardware dependent tasks. In some implementations, the instruction set(s) 940 include executable software defined by binary information stored in the form of electrical charge. In some implementations, the instruction set(s) 940 are software that is executable by the one or more processing units 902 to carry out one or more of the techniques described herein.

The instruction set(s) 940 include a content instruction set 942, a physiological tracking instruction set 944, a context instruction set 946, and a reading characteristics and interaction event instruction set 948. The instruction set(s) 940 may be embodied a single software executable or multiple software executables.

In some implementations, the content instruction set 942 is executable by the processing unit(s) 902 to provide and/or track content for display on a device. The content instruction set 942 may be configured to monitor and track the content over time (e.g., during an experience such as an education session) and/or to identify change events that occur within the content. In some implementations, the content instruction set 942 may be configured to inject change events into content (e.g., feedback mechanisms) using one or more of the techniques discussed herein or as otherwise may be appropriate. To these ends, in various implementations, the instruction includes instructions and/or logic therefor, and heuristics and metadata therefor.

In some implementations, the physiological tracking instruction set 944 is executable by the processing unit(s) 902 to track a user's physiological attributes (e.g., EEG amplitude/frequency, pupil modulation, eye gaze saccades, heart rate, EDA data, etc.) using one or more of the techniques discussed herein or as otherwise may be appropriate. To these ends, in various implementations, the instruction includes instructions and/or logic therefor, and heuristics and metadata therefor.

In some implementations, the context instruction set 946 is executable by the processing unit(s) 902 to determine a context of the experience and/or the environment (e.g., create a scene understanding to determine the objects or people in the content or in the environment, where the user is, what the user is watching, etc.) using one or more of the techniques discussed herein (e.g., object detection, facial recognition, etc.) or as otherwise may be appropriate. To these ends, in various implementations, the instruction includes instructions and/or logic therefor, and heuristics and metadata therefor.

In some implementations, the reading characteristics and interaction event instruction set 948 is executable by the processing unit(s) 902 to assess the physiological data with respect to a reading characteristic and determining whether to initiate an interaction event during the presentation of the content based on determining whether the user is reading the text or intends an interaction with the interactable element using one or more of the techniques discussed herein or as otherwise may be appropriate. To these ends, in various implementations, the instruction includes instructions and/or logic therefor, and heuristics and metadata therefor.

Although the instruction set(s) 940 are shown as residing on a single device, it should be understood that in other implementations, any combination of the elements may be located in separate computing devices. Moreover, FIG. 9 is intended more as functional description of the various features which are present in a particular implementation as opposed to a structural schematic of the implementations described herein. As recognized by those of ordinary skill in the art, items shown separately could be combined and some items could be separated. The actual number of instructions sets and how features are allocated among them may vary from one implementation to another and may depend in part on the particular combination of hardware, software, and/or firmware chosen for a particular implementation.

Figure 10:
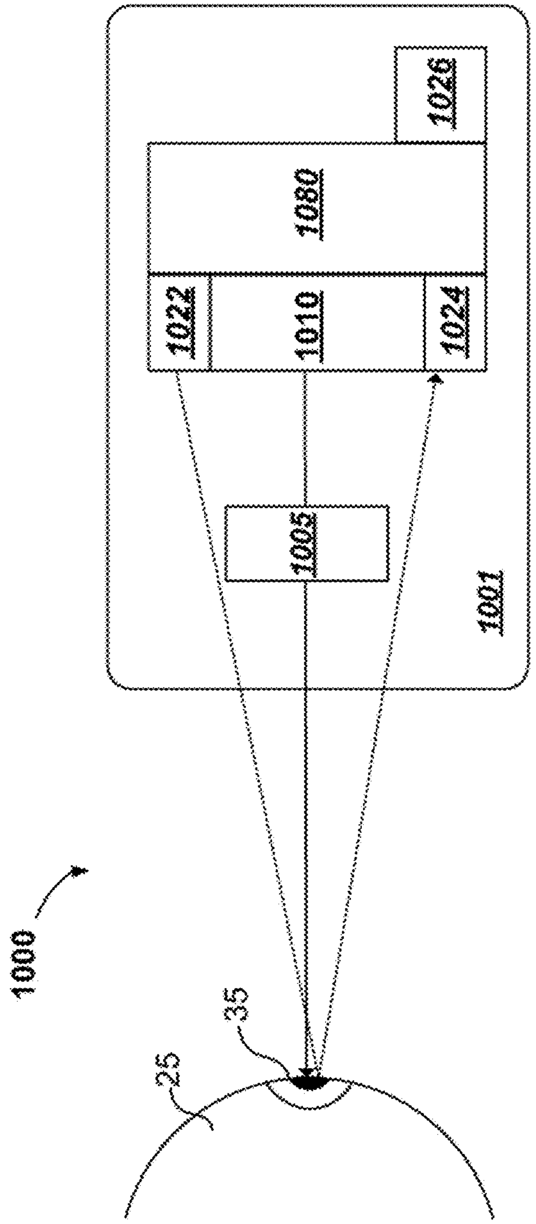
FIG. 10 illustrates an example head-mounted device (HMD) in accordance with some implementations.

FIG. 10 illustrates a block diagram of an exemplary head-mounted device 1000 in accordance with some implementations. The head-mounted device 1000 includes a housing 1001 (or enclosure) that houses various components of the head-mounted device 1000. The housing 1001 includes (or is coupled to) an eye pad (not shown) disposed at a proximal (to the user 25) end of the housing 1001. In various implementations, the eye pad is a plastic or rubber piece that comfortably and snugly keeps the head-mounted device 1000 in the proper position on the face of the user 25 (e.g., surrounding the eye of the user 25).

The housing 1001 houses a display 1010 that displays an image, emitting light towards or onto the eye of a user 25. In various implementations, the display 1010 emits the light through an eyepiece having one or more lenses 1005 that refracts the light emitted by the display 1010, making the display appear to the user 25 to be at a virtual distance farther than the actual distance from the eye to the display 1010. For the user 25 to be able to focus on the display 1010, in various implementations, the virtual distance is at least greater than a minimum focal distance of the eye (e.g., 8 cm). Further, in order to provide a better user experience, in various implementations, the virtual distance is greater than 1 meter.

Alternatively, in some embodiments, a display source and waveguides are utilized as opposed to the display 1010 and lenses 1005. A waveguide can produce a display from the display source appear to the user 25 to be at a virtual distance farther than the actual distance from the eye.

The housing 1001 also houses a tracking system including one or more light sources 1022, camera 1024, and a controller 1080. The one or more light sources 1022 emit light onto the eye of the user 25 that reflects as a light pattern (e.g., a circle of glints) that can be detected by the camera 1024. Based on the light pattern, the controller 1080 can determine an eye tracking characteristic of the user 25. For example, the controller 1080 can determine a gaze direction and/or a blinking state (eyes open or eyes closed) of the user 25. As another example, the controller 1080 can determine a pupil center, a pupil size, or a point of regard. Thus, in various implementations, the light is emitted by the one or more light sources 1022, reflects off the eye of the user 25, and is detected by the camera 1024. In various implementations, the light from the eye of the user 25 is reflected off a hot mirror or passed through an eyepiece before reaching the camera 1024.

The housing 1001 also houses an audio system that includes one or more audio source(s) 1026 that the controller 1080 can utilize for providing audio to the user per the techniques described herein. For example, audio source(s) 1026 can provide sound for both background sound and the feedback mechanism that can be presented spatially in a 3D coordinate system. The audio source(s) 1026 can include a speaker, a connection to an external speaker system such as headphones, or an external speaker connected via a wireless connection.

The display 1010 emits light in a first wavelength range and the one or more light sources 1022 emit light in a second wavelength range. Similarly, the camera 1024 detects light in the second wavelength range. In various implementations, the first wavelength range is a visible wavelength range (e.g., a wavelength range within the visible spectrum of approximately 410-700 nm) and the second wavelength range is a near-infrared wavelength range (e.g., a wavelength range within the near-infrared spectrum of approximately 700-1410 nm).

In various implementations, eye tracking (or, in particular, a determined gaze direction) is used to enable user interaction (e.g., the user 25 selects an option on the display 1010 by looking at it), provide foveated rendering (e.g., present a higher resolution in an area of the display 1010 the user 25 is looking at and a lower resolution elsewhere on the display 1010), or correct distortions (e.g., for images to be provided on the display 1010).

In various implementations, the one or more light sources 1022 emit light towards the eye of the user 25 which reflects in the form of a plurality of glints.

In various implementations, the camera 1024 is a frame/shutter-based camera that, at a particular point in time or multiple points in time at a frame rate, generates an image of the eye of the user 25. Each image includes a matrix of pixel values corresponding to pixels of the image which correspond to locations of a matrix of light sensors of the camera. In implementations, each image is used to measure or track pupil dilation by measuring a change of the pixel intensities associated with one or both of a user's pupils.

In various implementations, the camera 1024 is an event camera including a plurality of light sensors (e.g., a matrix of light sensors) at a plurality of respective locations that, in response to a particular light sensor detecting a change in intensity of light, generates an event message indicating a particular location of the particular light sensor.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

The described technology may gather and use information from various sources. This information may, in some instances, include personal information that identifies or may be used to locate or contact a specific individual. This personal information may include demographic data, location data, telephone numbers, email addresses, date of birth, social media account names, work or home addresses, data or records associated with a user's health or fitness level, or other personal or identifying information.

The collection, storage, transfer, disclosure, analysis, or other use of personal information should comply with well-established privacy policies or practices. Privacy policies and practices that are generally recognized as meeting or exceeding industry or governmental requirements should be implemented and used. Personal information should be collected for legitimate and reasonable uses and not shared or sold outside of those uses. The collection or sharing of information should occur after receipt of the user's informed consent.

It is contemplated that, in some instances, users may selectively prevent the use of, or access to, personal information. Hardware or software features may be provided to prevent or block access to personal information. Personal information should be handled to reduce the risk of unintentional or unauthorized access or use. Risk can be reduced by limiting the collection of data and deleting the data once it is no longer needed. When applicable, data de-identification may be used to protect a user's privacy.

Although the described technology may broadly include the use of personal information, it may be implemented without accessing such personal information. In other words, the present technology may not be rendered inoperable due to the lack of some or all of such personal information.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various objects, these objects should not be limited by these terms. These terms are only used to distinguish one object from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, objects, or components, but do not preclude the presence or addition of one or more other features, integers, steps, operations, objects, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:

at a device comprising a processor:

obtaining physiological data associated with an eye of a user during presentation of content, wherein the content comprises text that includes an interactable element embedded within or proximate to the text;

determining whether the user is reading a portion of the text or intends an interaction with the portion of the text that includes the interactable element based on an assessment of the physiological data with respect to a reading characteristic, including detecting that the user is transitioning from reading the portion of the text to interacting with the portion of the text, wherein, if the physiological data satisfies a first criterion, the user is determined to be reading the portion of the text and, if the physiological data satisfies a second criterion, the user is determined to be performing the interaction with the portion of the text that is different than reading the portion of the text; and in accordance with a determination that the user intends the interaction with the portion of the text that includes the interactable element, initiating an interaction event associated with the portion of the text.

2. The method of claim 1, wherein the interaction event is embedded within the portion of the text.

3. The method of claim 1, further comprising:

in accordance with a determination that the user is reading the portion of the text, forgoing initiating the interaction event associated with the portion of the text.

4. The method of claim 1, wherein the first criterion is associated with a reading characteristic that comprises a reading pace of the text by the user.

5. The method of claim 1, wherein determining whether the user is reading the portion of the text or intends an interaction with the portion of the text that includes the interactable element based on the assessment comprises:

determining a transition detection from the user reading the text to the user intending the interaction with the portion of the text that includes the interactable element.

6. The method of claim 1, wherein determining whether the user is reading a portion of the text or intends an interaction with the portion of the text that includes the interactable element based on the assessment comprises:

determining a reading pace of the user from the user reading the text; and comparing the reading pace to a threshold.

7. The method of claim 1, wherein determining whether the user is reading a portion of the text or intends an interaction with the portion of the text that includes the interactable element based on the assessment comprises:

detecting that the user is transitioning from reading the portion of the text to interacting with the portion of the text.

8. The method of claim 1, wherein determining whether the user is reading a portion of the text or intends an interaction with the portion of the text that includes the interactable element based on an assessment comprises:

determining scene-induced pupil response variation characteristics for the portion of the text; and determining that the user intends an interaction with the portion of the text that includes the interactable element based on the scene-induced pupil response variation characteristics for the portion of the text.

9. The method of claim 1, wherein an intent for the interaction is classified using a machine learning technique based on a pupillary response and the interaction with the portion of the text that includes the interactable element.

10. The method of claim 9, wherein the machine learning technique is refined based on at least one of a reading pace of the user, a detected transition from reading the text to an intent to interact with the portion of the text that includes the interactable element, and a detected intent of the user to cancel the interaction event.

11. The method of claim 1, further comprising:

adjusting content in response to initiating the interaction event.

12. The method of claim 1, further comprising:

determining that the user cancels the interaction event based on determining that the interaction event comprises a false positive activation based on a detection of an abnormal user action.

13. The method of claim 12, wherein the abnormal user action is:

an eye twitch;

an eye closing; or an eye squinting.

14. The method of claim 1, wherein the physiological data comprises an image of an eye or electrooculography (EOG) data.

15. The method of claim 1, wherein the physiological data comprises head movements of the user.

16. The method of claim 1, wherein the device is a head-mounted device (HMD).

17. The method of claim 1, wherein the presentation of content is an extended reality (XR) experience that is presented to the user.

18. A device comprising:

a non-transitory computer-readable storage medium; and one or more processors coupled to the non-transitory computer-readable storage medium, wherein the non-transitory computer-readable storage medium comprises program instructions that, when executed on the one or more processors, cause the one or more processors to perform operations comprising:

obtaining physiological data associated with an eye of a user during presentation of content, wherein the content comprises text that includes an interactable element embedded within or proximate to the text;

determining whether the user is reading a portion of the text or intends an interaction with the portion of the text that includes the interactable element based on an assessment of the physiological data with respect to a reading characteristic, including detecting that the user is transitioning from reading the portion of the text to interacting with the portion of the text, wherein, if the physiological data satisfies a first criterion, the user is determined to be reading the portion of the text and, if the physiological data satisfies a second criterion, the user is determined to be performing the interaction with the portion of the text that is different than reading the portion of the text; and in accordance with a determination that the user intends the interaction with the portion of the text that includes the interactable element, initiating an interaction event associated with the portion of the text.

19. The device of claim 18, wherein the interaction event is embedded within the portion of the text.

20. A non-transitory computer-readable storage medium, storing program instructions executable on a device to perform operations comprising:

obtaining physiological data associated with an eye of a user during presentation of content, wherein the content comprises text that includes an interactable element embedded within or proximate to the text;

determining whether the user is reading a portion of the text or intends an interaction with the portion of the text that includes the interactable element based on an assessment of the physiological data with respect to a reading characteristic, including detecting that the user is transitioning from reading the portion of the text to interacting with the portion of the text, wherein, if the physiological data satisfies a first criterion, the user is determined to be reading the portion of the text and, if the physiological data satisfies a second criterion, the user is determined to be performing the interaction with the portion of the text that is different than reading the portion of the text; and in accordance with a determination that the user intends the interaction with the portion of the text that includes the interactable element, initiating an interaction event associated with the portion of the text.

* * * * *